(12) United States Patent
Beckham et al.

(10) Patent No.: US 11,781,107 B2
(45) Date of Patent: Oct. 10, 2023

(54) MICROORGANISMS ENGINEERED FOR MUCONATE PRODUCTION

(71) Applicants: Alliance for Sustainable Energy, LLC, Golden, CO (US); UT-Battelle, LLC, Oak Ridge, TN (US)

(72) Inventors: Gregg Tyler Beckham, Golden, CO (US); Christopher W. Johnson, Denver, CO (US); Allison Jean Zimont Werner, Denver, CO (US); Davinia Salvachúa Rodríguez, Golden, CO (US); Daniel A. Jacobson, Oak Ridge, TN (US); Erica Teixeira Prates, Oak Ridge, TN (US); Elsayed Tharwat Tolba Mohamed, Helsingborg (SE); Adam Michael Feist, Oakland, CA (US)

(73) Assignees: Alliance for Sustainable Energy, LLC, Golden, CO (US); UT-Battelle, LLC, Oak Ridge, TN (US)

( * ) Notice: Subject to any disclaimer, the term of this patent is extended or adjusted under 35 U.S.C. 154(b) by 236 days.

(21) Appl. No.: 17/184,580

(22) Filed: Feb. 24, 2021

(65) Prior Publication Data
US 2021/0261911 A1 Aug. 26, 2021

Related U.S. Application Data

(60) Provisional application No. 62/980,634, filed on Feb. 24, 2020.

(51) Int. Cl.
*C12N 1/20* (2006.01)
*C12N 15/78* (2006.01)
*C12R 1/38* (2006.01)

(52) U.S. Cl.
CPC ............. *C12N 1/205* (2021.05); *C12N 15/78* (2013.01); *C12R 2001/38* (2021.05)

(58) Field of Classification Search
CPC .... C12N 1/205; C12N 15/78; C12R 2001/38; C12R 2001/40
See application file for complete search history.

(56) References Cited

U.S. PATENT DOCUMENTS

| | | | |
|---|---|---|---|
| 4,952,501 A | 8/1990 | Jasin et al. | |
| 10,017,792 B2* | 7/2018 | Beckham | ................ C07C 51/43 |
| 10,253,338 B2* | 4/2019 | Beckham | ........ C12Y 401/01045 |
| 10,738,333 B2* | 8/2020 | Elmore | ..................... C12P 7/48 |
| 11,326,151 B2* | 5/2022 | Guss | ........................ C12N 9/001 |
| 11,326,190 B2* | 5/2022 | Beckham | ....... C12Y 401/01044 |

OTHER PUBLICATIONS

Masuda et al. 1995 (Outer Membrane Proteins Responsible for Multiple Drug Resistance in Pseudomonas aeruginosa; Antimicrobial Agents and Chemotherapy 39:3: 645-649). (Year: 1995).*
Vardon et al. 2015 (Adipic acid production from lignin (Energy & Environmental Science 8:617-628). (Year: 2015).*
Basler et al., "A Pseudomonas putida efflux pump acts on short-chain alcohols", Biotechnology for Biofuels, 2018, vol. 11, No. 36, pp. 1-10.
Blanco-Romero et al., "Genome-wide analysis of the FleQ direct regulon in Pseudomonas fluorescens F113 and Pseudomonas putida KT2440", Scientific Reports, 2018, vol. 8, No. 13145, pp. 1-13.
Calero et al. "Genome-wide identification of tolerance mechanisms toward p-coumaric acid in Pseudomonas putida", Biotechnology and Bioengineering, Nov. 2017, vol. 115, No. 3, pp. 762-774.
Calero et al., "Chasing bacterial chassis for metabolic engineering: a perspective review from classical to non-traditional microorganisms", Microbial Biotechnology, Jan. 2019, vol. 12, No. 1, pp. 98-124.
Daniels et al., "Domain cross-talk during effector binding to the multidrug binding TTGR regulator", Journal of Biological Chemistry, Jul. 2010, vol. 285, No. 28, pp. 21372-21381.
Dvořák et al., "Bioremediation 3.0: Engineering pollutant-removing bacteria in the times of systemic biology", Biotechnology Advances, Nov. 2017, vol. 35, No. 7, pp. 845-866.
Fernandez et al., "Mechanisms of resistance to chloramphenicol in Pseudomonas putida KT2440", Antimicrobial Agents and Chemotherapy, 2012, vol. 56, No. 2, pp. 1001-1009.
Godoy et al., "Characterization of the RND family of multidrug efflux pumps: in silico to in vivo confirmation of four functionally distinct subgroups", Microbial Biotechnology, Nov. 2010, vol. 3, No. 6, pp. 691-700.
Johnson et al., "Eliminating a global regulator of carbon catabolite repression enhances the conversion of aromatic lignin monomers to muconate in Pseudomonas putida KT2440", Metabolic Engineering Communications, Dec. 2017, vol. 5, pp. 19-25.
Kamimura et al., "Bacterial catabolismof lignin-derived aromatics: New findings in a recent decade: Update on bacterial lignin catabolism", Environmental Microbiology Reports, Dec. 2017, vol. 9, No. 6, pp. 679-705.
Kim et al., "The Sensor Kinase GacS Negatively Regulates Flagellar Formation and Motility in a Biocontrol Bacterium, Pseudomonas chlororaphis O6", The Plant Pathology Journal, Jun. 2014, vol. 30, No. 2, pp. 215-219.
Kim et al., "Indole-Induced Activities of β-Lactamase and Efflux Pump Confer Ampicillin Resistance in Pseudomonas putida KT2440". Frontiers in Microbiology, Mar. 2017, vol. 8, No. 433, pp. 1-14.
Martinez-Gil et al., "Roles of cyclic Di-GMP and the Gac system in transcriptional control of the genes coding for the Pseudomonas putida adhesins LapA and LapF", Journal of Bacteriology, Apr. 2014, vol. 196, No. 8, pp. 1484-1495.
Mori et al., "Identification of the protocatechuate transporter gene in *Sphingobium* sp. strain SYK-6 and effects of overexpression on production of a value-added metabolite", Applied Microbiology and Biotechnology, Jun. 2018, vol. 102, No. 11, pp. 4807-481.

(Continued)

*Primary Examiner* — Mary Maille Lyons
(74) *Attorney, Agent, or Firm* — Michael A. McIntyre; Sam J. Barkley

(57) ABSTRACT

Disclosed herein are the genetically modified *Pseudomonas* with improved tolerance to hydroxycinnamic acids.

18 Claims, 23 Drawing Sheets
Specification includes a Sequence Listing.

(56) References Cited

OTHER PUBLICATIONS

Mori et al., "DdvK, a Novel Major Facilitator Superfamily Transporter Essential for 5,5'-Dehydrodivanillate Uptake by *Sphingobium* sp. Strain SYK-6", Applied and Environmental Microbiolgy, Oct. 2018, vol. 84, No. 20, pp. 1-16.

Nichols et al, "PcaK, a high-affinity permease for the aromatic compounds 4-hydroxybenzoate and protocatechuate from Pseudomonas putida", Journal of Bacteriology, Aug. 1997, vol. 179, No. 16, pp. 5056-5061.

Ramos et al., "Efflux pumps involved in toluene tolerance in Pseudomonas putida DOT-T1E", Journal of Bacterioogy, Jul. 1998, vol. 180, No. 13, pp. 3323-3329.

Ravi et al., "Conversion of lignin model compounds by Pseudomonas putida KT2440 and isolates from compost", Applied Microbiology and Biotechnology, Jun. 2017, vol. 101, No. 12, pp. 5059-5070.

Sainsbury et al., "Breaking Down Lignin to High-Value Chemicals: The Conversion of Lignocellulose to Vanillin in a Gene Deletion Mutant of *Rhodococcus jostii* RHA1", ACS Chemical Biology, 2013, vol. 8, No. 10, pp. 2151-2156.

Salvachúa et al., "Towards lignin consolidated bioprocessing: simultaneous lignin depolymerization and product generation by bacteria", Green Chemistry, 2015, vol. 17, No. 11, pp. 4951-4967.

Salvachúa et al., "Bioprocess development for muconic acid production from aromatic compounds and lignin", Green Chemistry, 2018, vol. 20, No. 18, pp. 5007-5019.

Salvachúa et al., "Metabolic engineering of Pseudomonas putida for increased polyhydroxyalkanoate production from lignin", Microbial Biotechnolgy, Jan. 2020, vol. 13, No. 1, pp. 290-298.

Teran et al., "Antibiotic-dependent induction of Pseudomonas putida DOT-T1E TtgABC efflux pump is mediated by the drug binding repressor TtgR", Antimicrobial Agents and Chemotherapy, Oct. 2003, vol. 47, No. 10, pp. 3067-3072.

\* cited by examiner

```
                         SEQUENCE LISTING

<160> NUMBER OF SEQ ID NOS: 14

<210> SEQ ID NO 1
<211> LENGTH: 1392
<212> TYPE: DNA
<213> ORGANISM: Pseudomonas putida

<400> SEQUENCE: 1
atgatcaagc cgttgaacgg ggtatgcctg cccctcatgg tgctttcgct gtgccattcc      60
gcctacgcgg ccagcccgct tgaagagagc cggccgggga ggccaggggc ccctcgctgg     120
atcgaggact accgctttct cgacgacccc gccaaggcca ctgccccttt cgatggcctg     180
cgctaccatc ggctgtcaga gtcggcctgg ctgcaactcg gggctgaggc ccgctaccgg     240
gccgatgctt cggacaaacc cttctttggc ctgcgcgggc tgaacgacga ttcctatctg     300
```

-continued

```
cagcaacggc tgcaggccca tgccgacctg cacctgttcg acgatgccgt gcgtaccttc      360
gtccaggtcg agaatacccg tgcctttggc aaggacttgt actcgcccaa tgatgaaagc      420
cgcaatgaag tgcgacaggc cttcgtcgat ttcaaccacg atttcgccgc cgggcgctat      480
accacacgcg taggtcgcca ggagatgggc ttcggcgacc aggtgttggt cacctaccgc      540
gacgcgccga acatccgcct gagcttcgac ggcgtgcgcg ccagcctcaa cctcaaggac      600
ggacgcaagc tggatgcatt cgctgtgcgc ccgctgaaaa ccggtgaaga cagttgggac      660
gatggcagca acaacaacat caaattctac ggcctctacg caccttgcc gctgtcggcg       720 tcgtggaaca tggacctgct agcctttggc ctggaaaccg acgaccgcac cctggccggc      780
gagtcgggtg acgagcagcg ctacactttc ggcacgcggc tgttcggccg ccatcaggca      840
ctggactgga gctggaacct cgtcgggcag accggccacc tgggcaacgc gtcgatccgc      900
gcctgggcgc tgtcgagcga cagcggcttc accttcaccc accctggca accgcgcctg      960 gccatgcgca tcgatgccgc aagcggcgac agtgacctgg cgacggaaa agtcggcacc      1020 ttcgacccgc tttacccacg caatggtgtc tatggcgaag ccagcctcac caccctgagc      1080
aacatcatcg tggtggggcc gaccttcggc ttctcgccct ggcgcacgct gcgcatcgag      1140
cccggcatct tcgaagtgtg gaaacagcgt gaggaagacg gcgtgtacat gcccggcatg      1200
agcatgctgg ccaacacccg cggcacgggt cgccatgtcg gtaccatcta ccgcgccagc      1260
acgcgctggc ttgccactcc caacctgacc ctggaccttg acctgaagta ctacgacgtg      1320
ggcacggcca tcaaggaggc tggcggcgaa gattcgtcgt ttgtctcagt acgcgccacg      1380
ttccgccttt ga                                                          1392
```

<210> SEQ ID NO 2
<211> LENGTH: 463
<212> TYPE: PRT
<213> ORGANISM: Pseudomonas putida

<400> SEQUENCE: 2

```
Met Ile Lys Pro Leu Asn Gly Val Cys Leu Pro Leu Met Val Leu Ser
1               5                   10                  15

Leu Cys His Ser Ala Tyr Ala Ala Ser Pro Leu Glu Glu Ser Arg Pro
                20                  25                  30

Gly Arg Pro Gly Ala Pro Arg Trp Ile Glu Asp Tyr Arg Phe Leu Asp
            35                  40                  45

Asp Pro Ala Lys Ala Thr Ala Pro Phe Asp Gly Leu Arg Tyr His Arg
        50                  55                  60

Leu Ser Glu Ser Ala Trp Leu Gln Leu Gly Ala Glu Ala Arg Tyr Arg
65                  70                  75                  80

Ala Asp Ala Ser Asp Lys Pro Phe Phe Gly Leu Arg Gly Leu Asn Asp
                85                  90                  95

Asp Ser Tyr Leu Gln Gln Arg Leu Gln Ala His Ala Asp Leu His Leu
                100                 105                 110

Phe Asp Asp Ala Val Arg Thr Phe Gln Val Glu Asn Thr Arg Ala
                115                 120                 125

Phe Gly Lys Asp Leu Tyr Ser Pro Asn Asp Glu Ser Arg Asn Glu Val
            130                 135                 140

Arg Gln Ala Phe Val Asp Phe Asn His Asp Phe Ala Ala Gly Arg Tyr
145                 150                 155                 160

Thr Thr Arg Val Gly Arg Gln Glu Met Gly Phe Gly Asp Gln Val Leu
                165                 170                 175
```

```
Val Thr Tyr Arg Asp Ala Pro Asn Ile Arg Leu Ser Phe Asp Gly Val
            180                 185                 190

Arg Ala Ser Leu Asn Leu Lys Asp Gly Arg Lys Leu Asp Ala Phe Ala
        195                 200                 205

Val Arg Pro Leu Lys Thr Gly Glu Asp Ser Trp Asp Asp Gly Ser Asn
210                 215                 220

Asn Asn Ile Lys Phe Tyr Gly Leu Tyr Gly Thr Leu Pro Leu Ser Ala
225                 230                 235                 240

Ser Trp Asn Met Asp Leu Leu Ala Phe Gly Leu Glu Thr Asp Asp Arg
                245                 250                 255

Thr Leu Ala Gly Glu Ser Gly Asp Glu Gln Arg Tyr Thr Phe Gly Thr
            260                 265                 270

Arg Leu Phe Gly Arg His Gln Ala Leu Asp Trp Ser Trp Asn Leu Val
        275                 280                 285

Gly Gln Thr Gly His Leu Gly Asn Ala Ser Ile Arg Ala Trp Ala Leu
    290                 295                 300

Ser Ser Asp Ser Gly Phe Thr Phe Thr His Pro Trp Gln Pro Arg Leu
305                 310                 315                 320

Ala Met Arg Ile Asp Ala Ala Ser Gly Asp Ser Asp Leu Gly Asp Gly
                325                 330                 335

Lys Val Gly Thr Phe Asp Pro Leu Tyr Pro Arg Asn Gly Val Tyr Gly
            340                 345                 350

Glu Ala Ser Leu Thr Thr Leu Ser Asn Ile Ile Val Val Gly Pro Thr
        355                 360                 365

Phe Gly Phe Ser Pro Trp Arg Thr Leu Arg Ile Glu Pro Gly Ile Phe
    370                 375                 380

Glu Val Trp Lys Gln Arg Glu Glu Asp Gly Val Tyr Met Pro Gly Met
385                 390                 395                 400

Ser Met Leu Ala Asn Thr Arg Gly Thr Gly Arg His Val Gly Thr Ile
                405                 410                 415

Tyr Arg Ala Ser Thr Arg Trp Leu Ala Thr Pro Asn Leu Thr Leu Asp
            420                 425                 430

Leu Asp Leu Lys Tyr Tyr Asp Val Gly Thr Ala Ile Lys Glu Ala Gly
        435                 440                 445

Gly Glu Asp Ser Ser Phe Val Ser Val Arg Ala Thr Phe Arg Leu
    450                 455                 460

<210> SEQ ID NO 3
<211> LENGTH: 19
<212> TYPE: DNA
<213> ORGANISM: Artificial Sequence
<220> FEATURE:
<223> OTHER INFORMATION: Primer CJ680

<400> SEQUENCE: 3
tttgtgatgc tcgtcaggg                                             19

<210> SEQ ID NO 4
<211> LENGTH: 19
<212> TYPE: DNA
<213> ORGANISM: Artificial Sequence
<220> FEATURE:
<223> OTHER INFORMATION: Primer CJ681

<400> SEQUENCE: 4
cttcccaacc ttaccagag                                             19
```

```
<210> SEQ ID NO 5
<211> LENGTH: 32
<212> TYPE: DNA
<213> ORGANISM: Artificial Sequence
<220> FEATURE:
<223> OTHER INFORMATION: Primer CJ791

<400> SEQUENCE: 5
acatgattac gaattccgga catcagcatc gc                                    32

<210> SEQ ID NO 6
<211> LENGTH: 37
<212> TYPE: DNA
<213> ORGANISM: Artificial Sequence
<220> FEATURE:
<223> OTHER INFORMATION: Primer CJ793

<400> SEQUENCE: 6
ttaaacactt gtttttataa ttgttcttac aaactgg                                37

<210> SEQ ID NO 7
<211> LENGTH: 41
<212> TYPE: DNA
<213> ORGANISM: Artificial Sequence
<220> FEATURE:
<223> OTHER INFORMATION: Primer CJ793

<400> SEQUENCE: 7
ttataaaaac aagtgtttaa acccacccga ccgataacaa c                          41

<210> SEQ ID NO 8
<211> LENGTH: 26
<212> TYPE: DNA
<213> ORGANISM: Artificial Sequence
<220> FEATURE:
<223> OTHER INFORMATION: Primer CJ794

<400> SEQUENCE: 8
tgccaagctt tcagcgacgc aaccgc                                           26

<210> SEQ ID NO 9
<211> LENGTH: 21
<212> TYPE: DNA
<213> ORGANISM: Artificial Sequence
<220> FEATURE:
<223> OTHER INFORMATION: Primer CJ795

<400> SEQUENCE: 9
gtctccgaca tcatgcccag c                                                21

<210> SEQ ID NO 10
<211> LENGTH: 22
<212> TYPE: DNA
<213> ORGANISM: Artificial Sequence
<220> FEATURE:
<223> OTHER INFORMATION: Primer CJ796

<400> SEQUENCE: 10
gtagaacacc gtacgccaac cg                                               22

<210> SEQ ID NO 11
<211> LENGTH: 23
<212> TYPE: DNA
<213> ORGANISM: Artificial Sequence
<220> FEATURE:
<223> OTHER INFORMATION: Primer TEAM-1640
```

```
<400> SEQUENCE: 11
acccaccgcc ctggtggtca acc                                              23

<210> SEQ ID NO 12
<211> LENGTH: 25
<212> TYPE: DNA
<213> ORGANISM: Artificial Sequence
<220> FEATURE:
<223> OTHER INFORMATION: Primer TEAM 1641

<400> SEQUENCE: 12
cagggatcag cgagcagccg ccaag                                            25

<210> SEQ ID NO 13
<211> LENGTH: 24
<212> TYPE: DNA
<213> ORGANISM: Artificial Sequence
<220> FEATURE:
<223> OTHER INFORMATION: Primer F-5'ttgAend

<400> SEQUENCE: 13
cgtcgaggtg aaggtcagcg atgc                                             24

<210> SEQ ID NO 14
<211> LENGTH: 25
<212> TYPE: DNA
<213> ORGANISM: Artificial Sequence
<220> FEATURE:
<223> OTHER INFORMATION: Primer RttgCbeg

<400> SEQUENCE: 14
ccgattgcgt cggcgagata agcag                                            25
```

MICROORGANISMS ENGINEERED FOR MUCONATE PRODUCTION

CROSS-REFERENCE TO RELATED APPLICATION

This application claims priority from U.S. Provisional Patent Application No. 62/980,634 filed on Feb. 24, 2020, the contents of which are incorporated herein by reference in their entirety.

CONTRACTUAL ORIGIN

This invention was made with government support under Contract No. DE-AC36-08GO28308 awarded by the Department of Energy. The United States Government has rights in this invention pursuant to Contract No. DE-AC05-00OR22725 between the United States Department of Energy and UT-Battelle, LLC. The government has certain rights in the invention.

SUMMARY

In an aspect disclosed herein is a genetically modified *Pseudomonas* comprising a mutation of a gene encoding a cell membrane protein wherein the modification improves tolerance to hydroxycinnamic acid relative to the non-genetically modified *Pseudomonas*. A method for lignin valorization, the method comprising: converting a hydroxycinnamic acid to muconate utilizing a genetically modified *Pseudomonas* comprising: a modification of a gene encoding a cell membrane protein; wherein the modification increases the uptake of the hydroxycinnamic acid relative to the uptake of a non-genetically modified *Pseudomonas*.

SEQUENCE LISTING

The instant application contains a Sequence Listing which has been submitted via EFS-web and is hereby incorporated by reference in its entirety. The ASCII copy as filed herewith was created on 24 Feb. 2021. The ASCII copy as filed herewith is named NREL 20-48_ST25.txt, is 9 kilobytes in size and is submitted with the instant application.

BRIEF DESCRIPTION OF DRAWINGS

Some embodiments are illustrated in referenced figures of the drawings. It is intended that the embodiments and figures disclosed herein are to be considered illustrative rather than limiting.

(FIG. 3A) Duration of each experiment in number of passages and cumulative cell divisions (CCD). (FIG. 3B) Substrate concentration at the start ($C_{initial}$) and end ($C_{final}$) of each experiment, and the fold-change increase from $t_0$ to $t_f$. For the pCA+FA conditions, substrate concentration is presented as a sum where each individual compound is present in a 1:1 mass ratio. (FIG. 3C) Bacterial growth rate at the start ($\mu_{initial}$) and end ($\mu_{final}$) of each experiment. Error bars represent the standard deviation of biological replicates (n=6 for pCA, FA, and pCA+FA, n=3 for glucose). TALE: Tolerance adaptive laboratory evolution; ALE: adaptive laboratory evolution.

(FIG. 7A) Overview of mutations in CJ782 and TALE endpoint populations tested here. Mutations are depicted for those which are fully fixed in a population; details on each strain can be found in Table 2. Deletions are denoted with an Δ; single nucleotide polymorphisms (SNPs) in ttgB and sucA ORFs are denoted with the AA1:position:AA2 notation; SNPs in the intergenic region between PP_5245 and kefB-III are denoted with nucleotide→nucleotide notation. Growth rate and lag phase of wild-type *P. putida* (WT), *P. putida* ΔPP_3350 (CJ782), and three TALE endpoint populations (TALE #7, #23, and #25) in (a) 10 g/L or 20 g/L pCA, (FIG. 7B) 10 g/L or 30 g/L FA, (FIG. 7C) 5 g/L pCA plus 5 g/L FA (10 g/L total) or 10 g/L pCA plus 10 g/L FA (20 g/L total), and (FIG. 7D) 20 g/L pCA+FA (10 g/L of each compound). Cells were cultivated in duplicate in M9 minimal media supplemented with the specified amount of aromatic compound. Error bars represent the absolute difference of two biological replicates.

DETAILED DESCRIPTION

Figure 1:
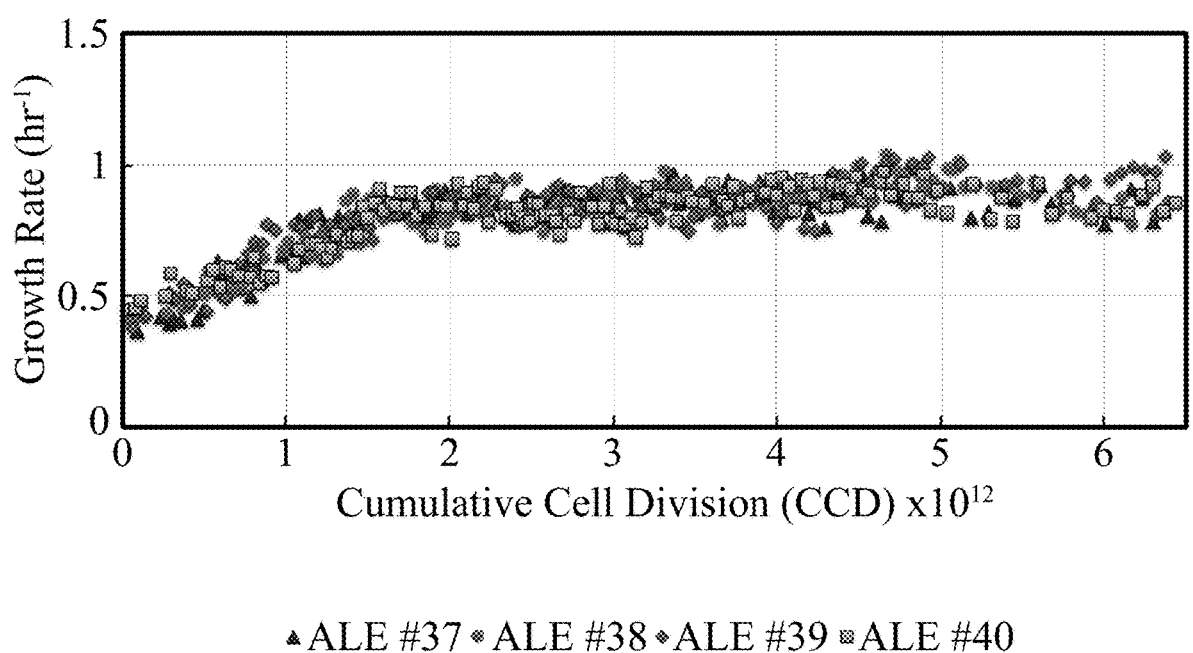
FIG. 1 depicts fitness trajectories of the ALE experiment on glucose. Depicted are the fitness trajectories of evolved *P. puitda* (growth rate, $h^{-1}$) in a static concentration of 10 g/L glucose over the cumulative cell divisions (CCD). Each of four biological replicates of the glucose ALE experiment are plotted.
Figure 2A:
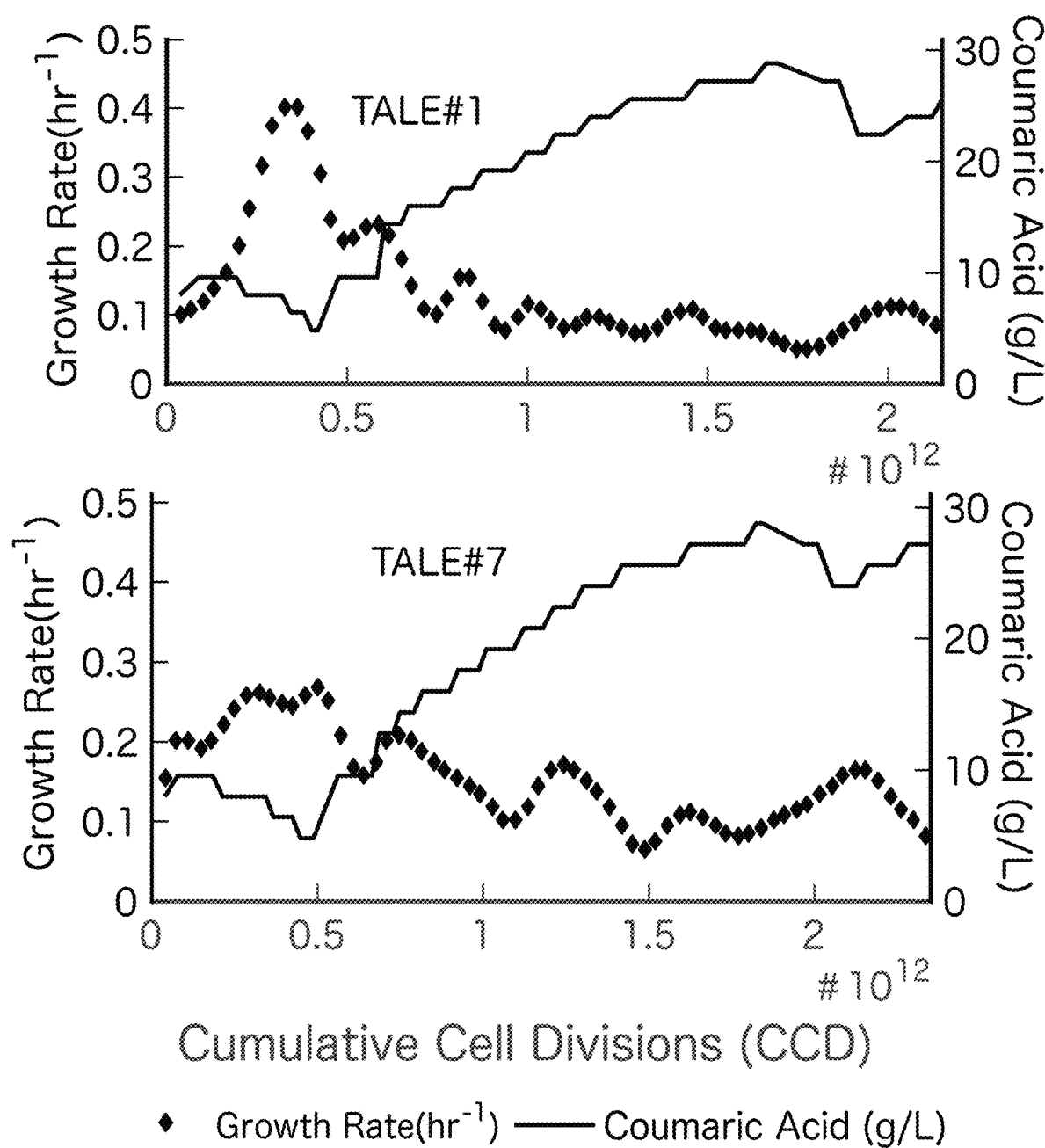
FIGS. 2A through 2I depict representative trajectories of population fitness and aromatic acid concentrations over the course of TALE experiments. Depicted are the fitness trajectories of evolved *P. putida* (growth rate, $h^{-1}$) as a function of the increasing hydroxycinnamic acid concentration over the course of the TALE experiments as a function of the cumulative cells division (CCD) for (FIGS. 2A, 2B, and 2C) pCA TALEs #1, #3, #5, #7, #9, and #11, (FIGS. 2D, 2E, and 2F) FA TALEs #13, #15, #17, #19, #21, and #23, and (FIGS. 2G, 2H, and 2I) pCA+FA TALEs (equivalent mass pCA and FA, the sum is plotted) #25, #27, #29, #31, #33, and #35. The concentration of each aromatic acid is shown as an orange line and growth rate is shown as a blue diamond.
Figure 2B:
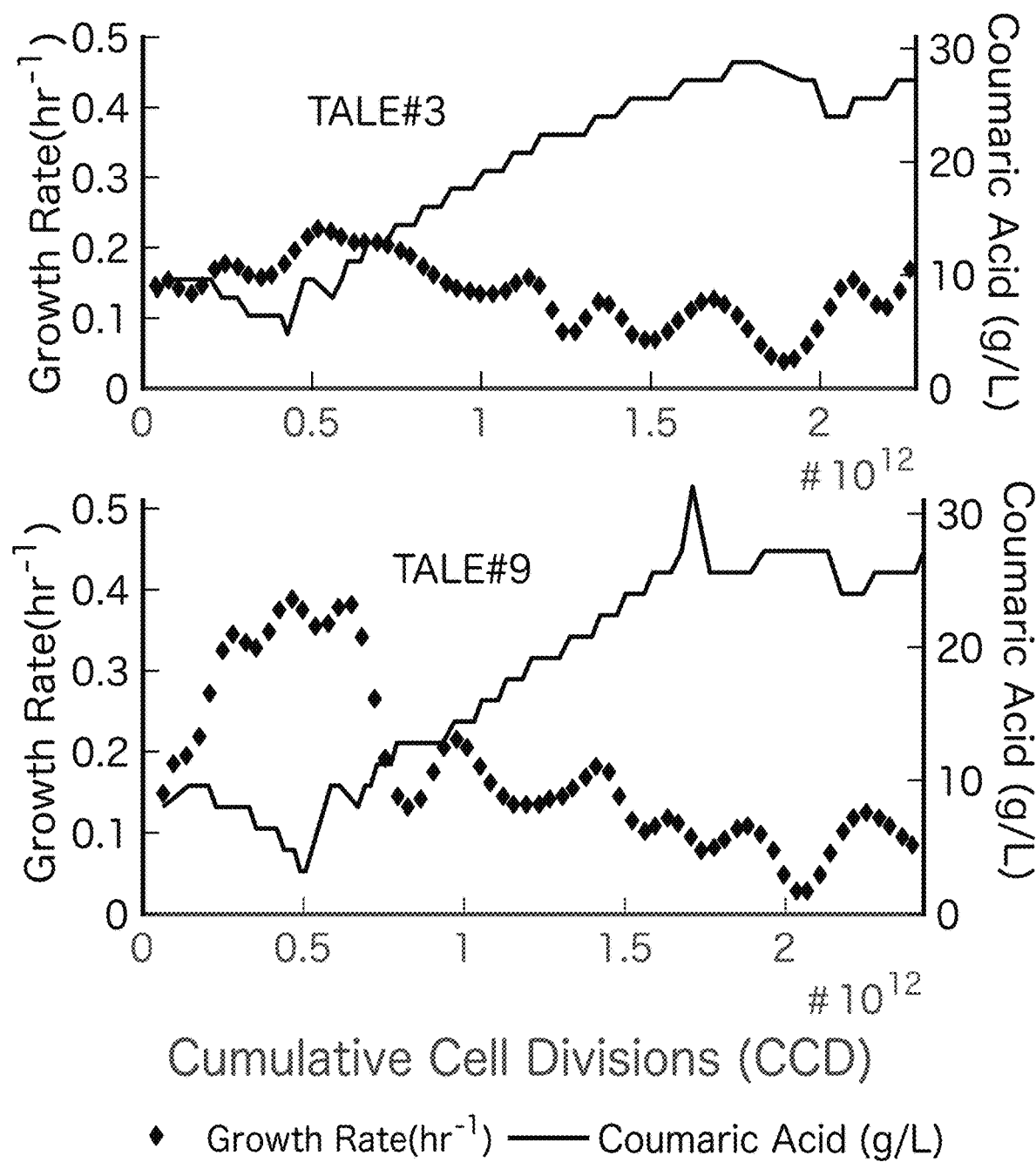
Figure 2C:
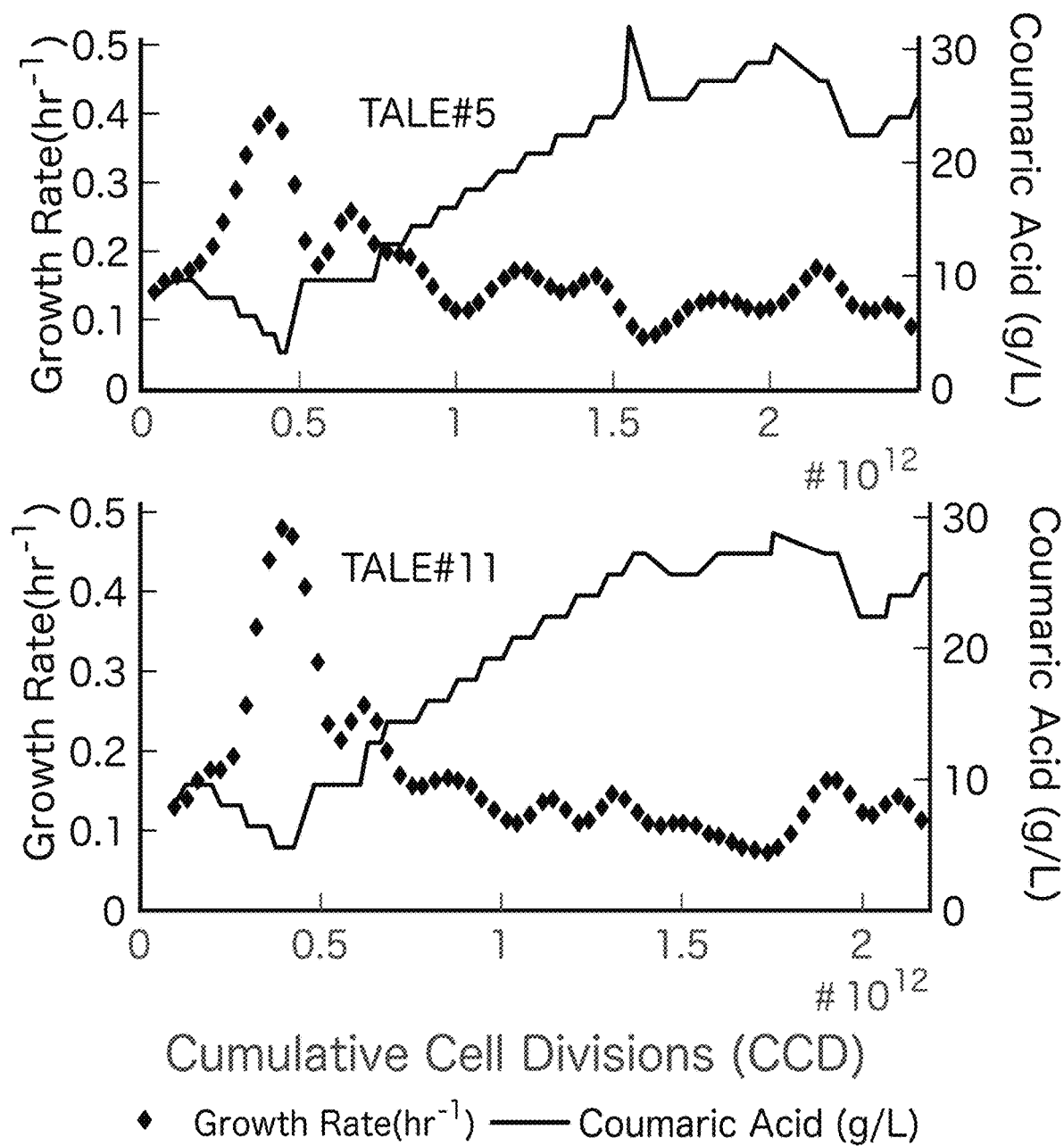
Figure 2D:
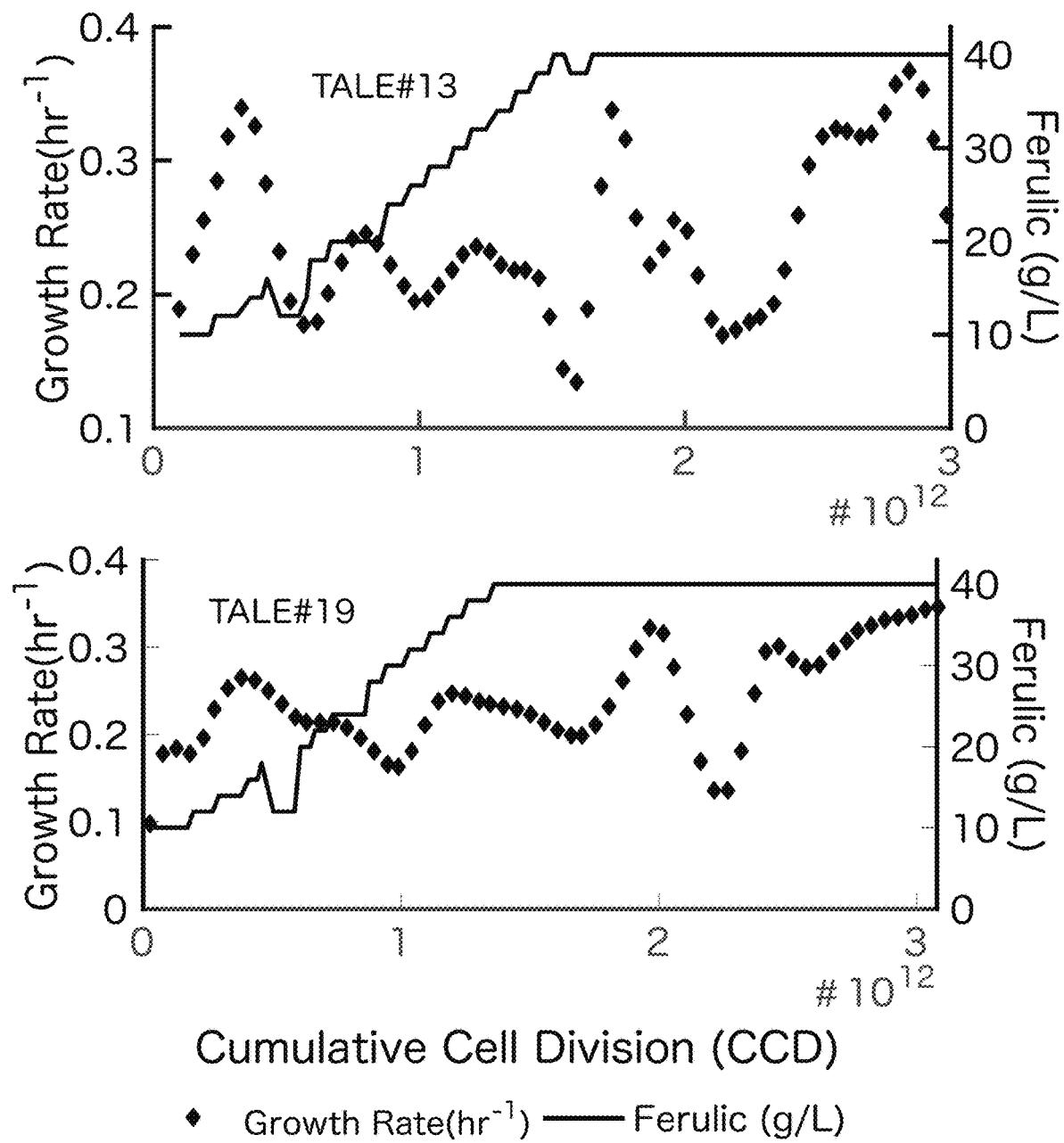
Figure 2E:
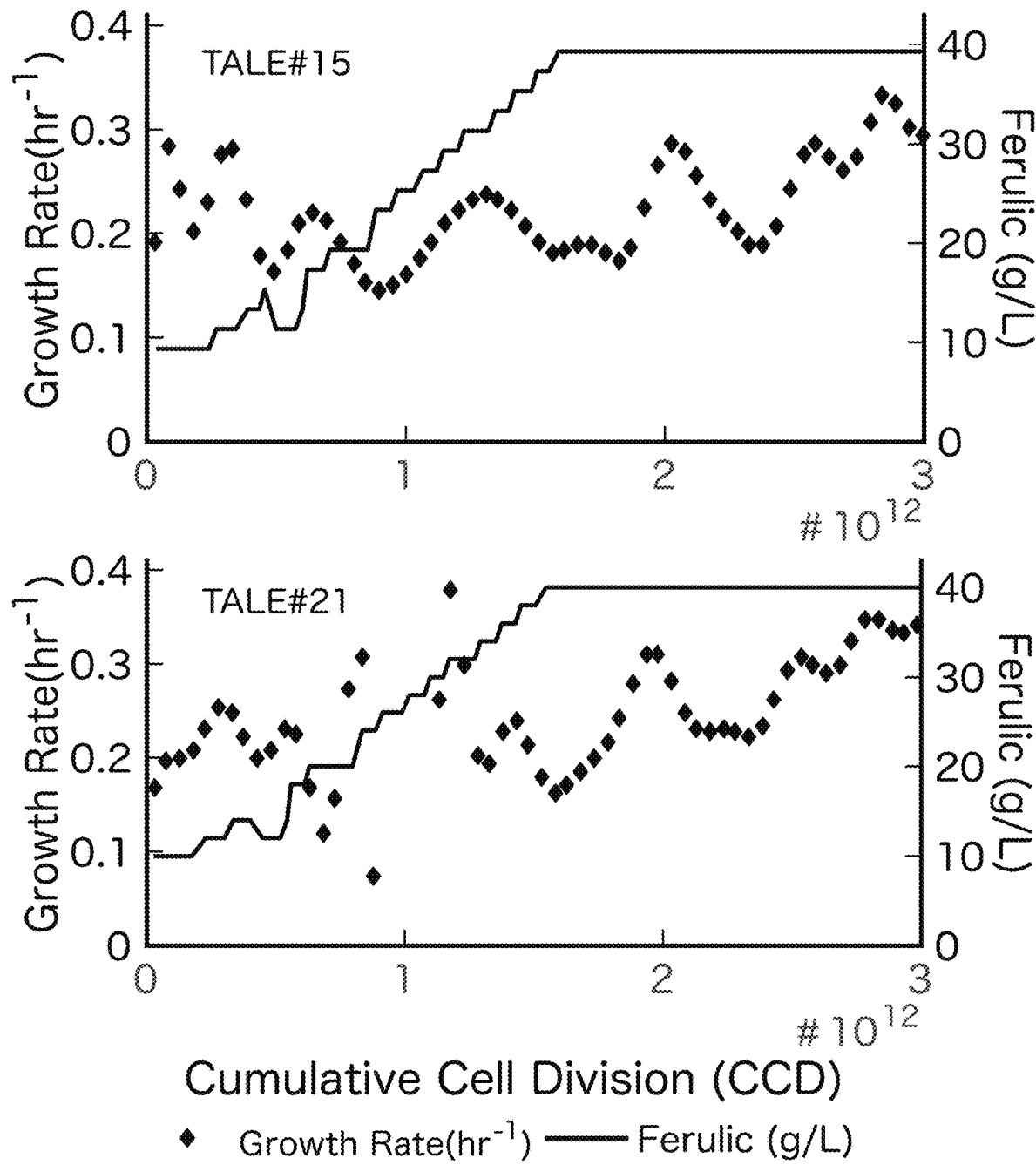
Figure 2F:
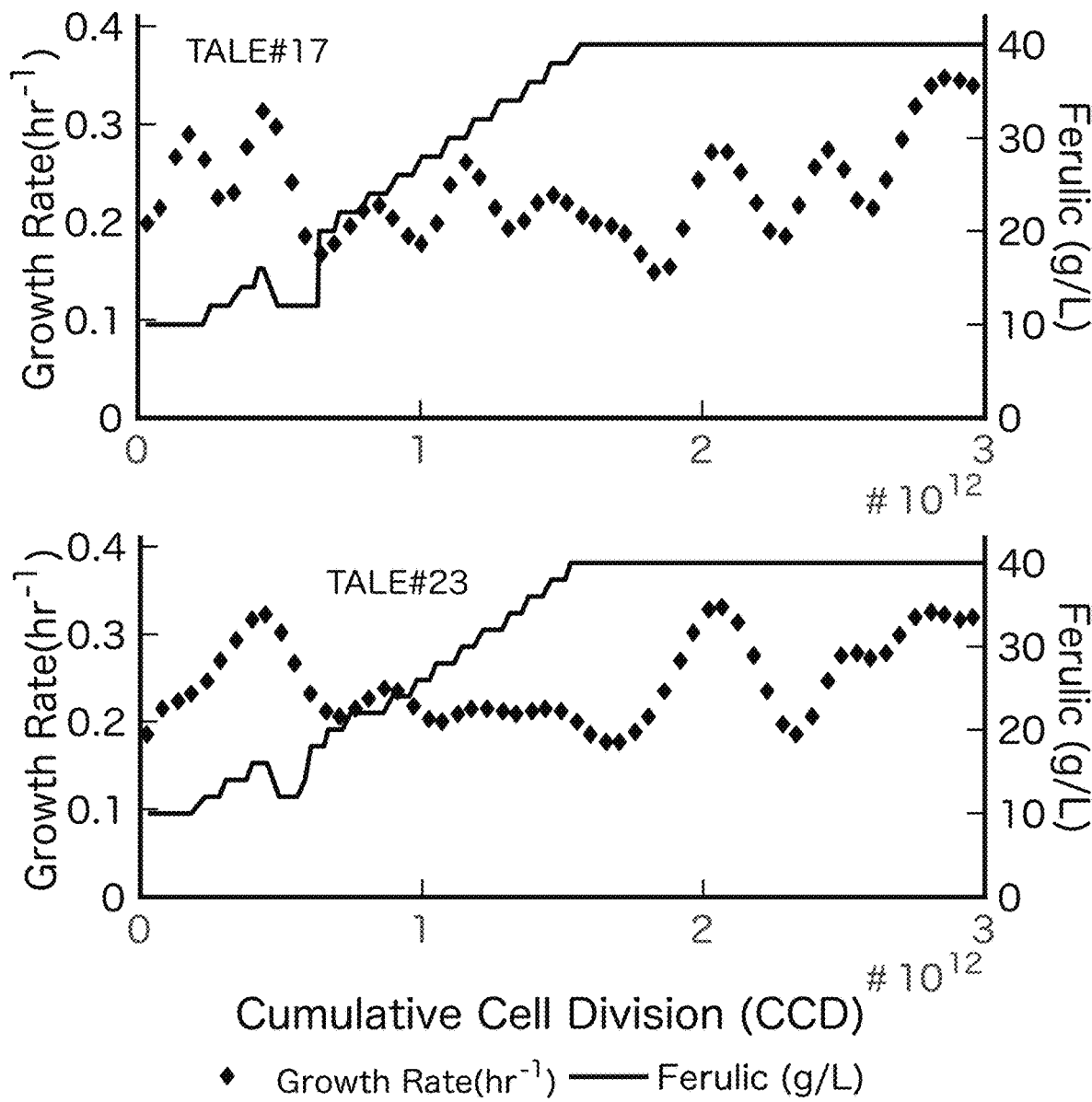
Figure 2G:
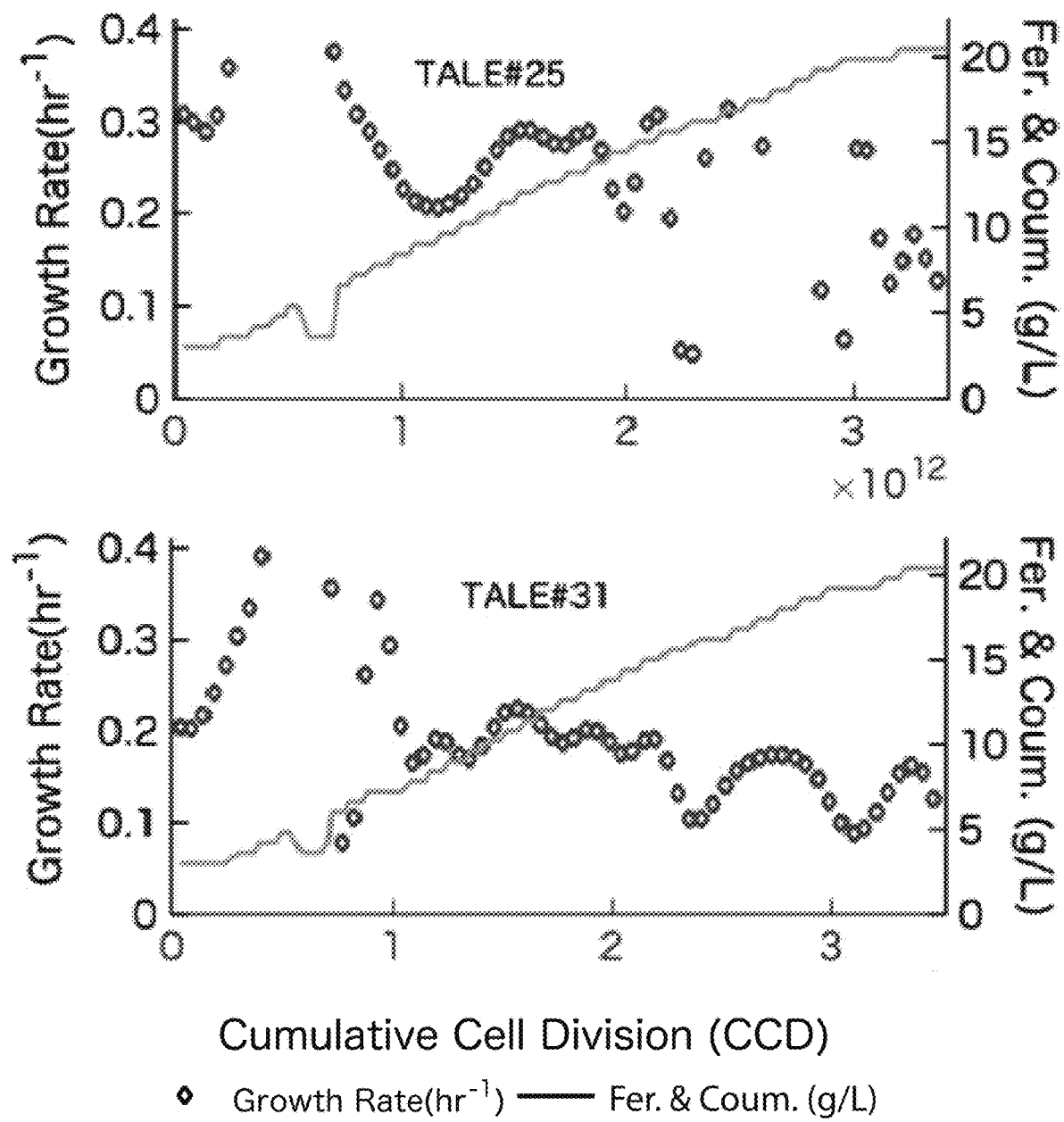
Figure 2H:
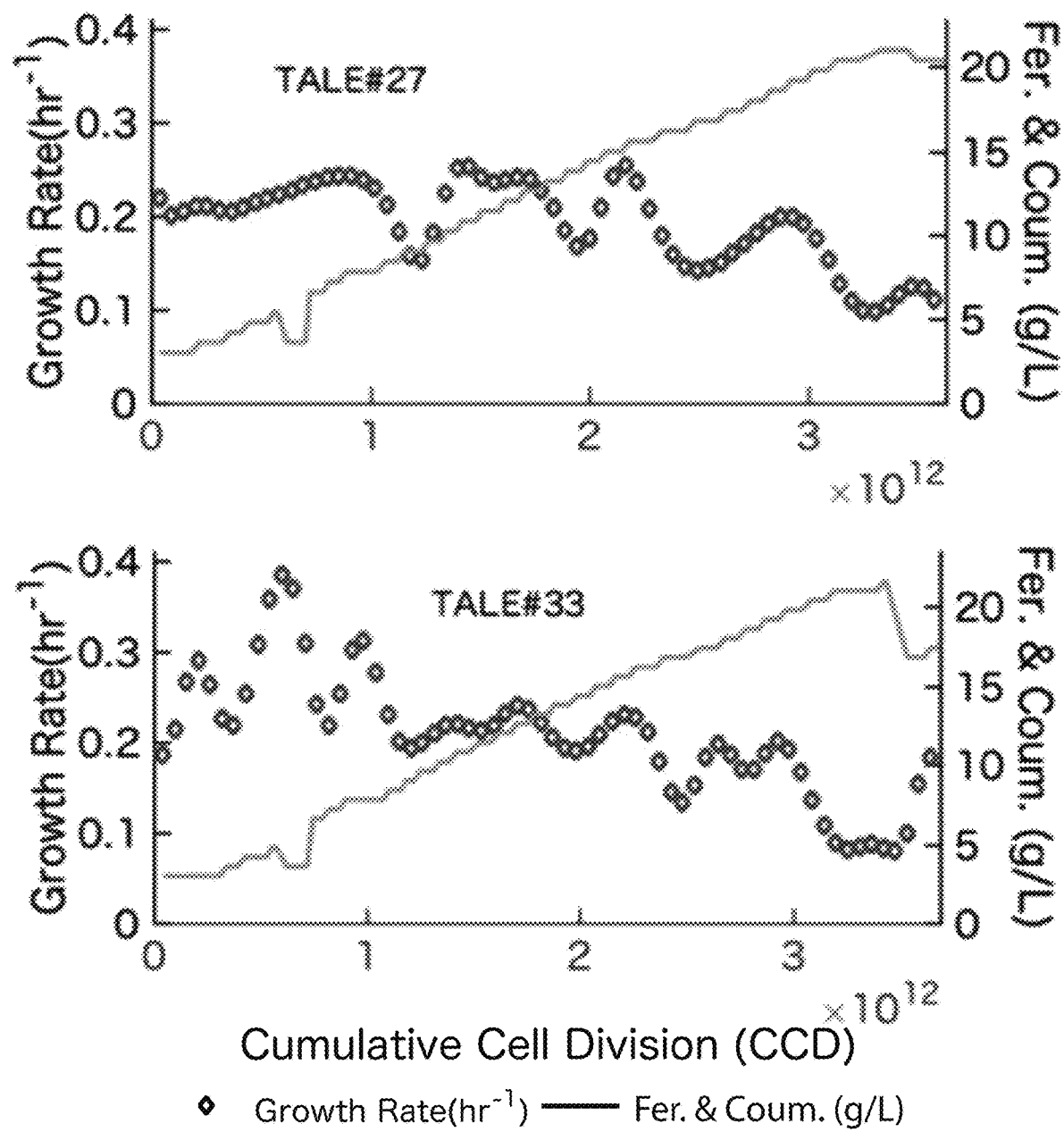
Figure 2I:
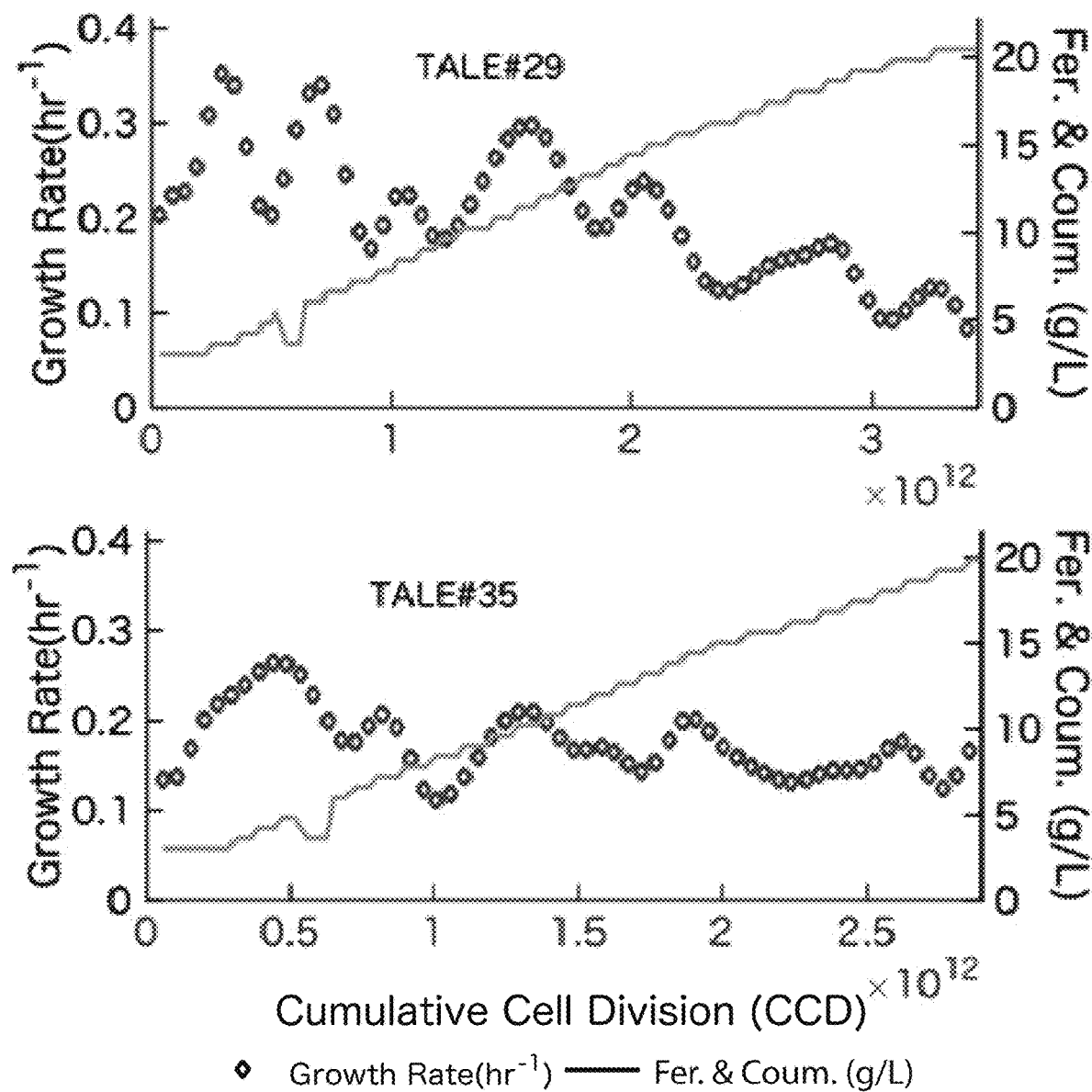

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

sdfsdf A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated and/or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, and/or termination of transcription. Suitable regulatory sequences include any sequence that can function in a host cell or organism into which the recombinant nucleic acid molecule is to be introduced, including those that control transcription initiation, such as promoter, enhancer, terminator, operator, and/or repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

SEQ ID NOs: 1-2 provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library) and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T. viride, T. koningii,* or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori,* or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, *miscanthus*, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC.

The nucleic acid molecules described herein encode the proteins with amino acid sequences such as those represented by some of the SEQ ID NOs presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein or may include up to a certain integer number of amino acid alterations. Such protein or polypeptide variants retain functionality as enzymes, and include mutants differing by the addition, deletion, or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Among other things, the present disclosure relates to engineering microorganisms to have the deletion or a modification of a gene encoding a membrane porin, with one example including the hypothetical protein PP_3350, also called NCBI-Protein NP_745490. As shown herein, these mutations affect the uptake of coumarate and ferulate and their conversion to muconate. In an embodiment, the nucleotide sequence of the gene encoding for hypothetical protein PP_3350 is SEQ ID NO: 1. In an embodiment, the hypothetical protein PP_3350 has an amino acid sequence that is SEQ ID NO: 2. These mutations remove the membrane transfer bottle-neck of substrates (e.g., coumarate and ferulate) into the microorganism allowing faster conversion of the substrates to the desired target molecule (e.g., muconate). As shown herein, one example of a microorganism that has been successfully engineered for enhanced tolerance to high concentrations of coumarate and/or ferulate is *Pseudomonas putida*. Such modified organisms may dramatically improve large-scale fermentation processes by, for example, allowing higher concentration of substrates, shorter batch times, and increased muconate production rates on a per unit volume basis.

*Pseudomonas putida* KT2440 is a promising bacterial chassis for the conversion of lignin-derived aromatic compound mixtures to high-value products. Despite the inherent robustness of this strain, improvement to both aromatic catabolic rates and toxicity tolerance of *P. putida* will be required to achieve industrially relevant bioprocess performance. Described herein is a tolerance adaptive laboratory evolution (TALE) approach using increasing concentrations of the plant-derived, hydroxycinnamic acids, p-coumaric acid (pCA), ferulic acid (FA), and an equal mass mixture of pCA and FA (pCA+FA). After 300-600 passages in each TALE line, evolved *P. putida* demonstrated increased tolerance to pCA, measured by a 3.3-fold increase in the maximum substrate concentration where growth was enabled, and a 37 hour decrease in lag phase, both at 20 g/L pCA. For FA, substrate utilization and tolerance were both improved; namely, evolved *P. putida* displayed growth on a 5-fold increase in FA concentration and a 2.4-fold increase in growth rate at 30 g/L FA.

Whole genome resequencing of intermediate and final evolved *P. putida* populations revealed several non-intuitive genetic targets underlying these aromatic catabolic and toxicity tolerance enhancements. PP_3350 was among the most frequently mutated genes and the beneficial contributions of this mutation was verified in vivo with single gene knockouts. Deletion of PP_3350, encoding a hypothetical protein, fully recapitulated the improved toxicity tolerance to high concentrations of pCA but not the improved growth rate in high concentrations of FA. The work described herein demonstrates improved microbial fitness, in regard to both tolerance and utilization of at least two hydroxycinnamic acids (e.g., coumarate and ferulate) via TALE and presents new targets towards improving *P. putida* for microbial lignin valorization.

As shown herein, adaptive laboratory evolution (ALE) can be an efficient approach that has proven useful for overcoming substrate toxicity, improving substrate consumption rates, and improving overall strain fitness. In the present disclosure, both the toxicity tolerance and consumption rates of pCA and FA are addressed by utilizing a systematic ALE strategy, tolerance adaptive laboratory evolution (TALE), to generate *P. putida* strains capable of growing at elevated hydroxycinnamic acid concentrations. Specifically, cells were continuously evolved in independent biological replicates under increasing levels of pCA, FA, and an equal mass ratio of both acids (hereafter referred to as pCA+FA). In addition, ALE was applied evolve *P. putida* in a static concentration of glucose as a control to enable identification of general adaptive mutations to media components and/or the cultivation conditions as opposed to the aromatic substrate(s) (FIG. 1). Cell populations and single isolates were selected from both TALE and ALE experiments at intermediate and endpoints to identify causal mutations. Endpoint populations were characterized in terms of their growths rates and tolerance levels. Through construction of genetic knockouts in a wild-type *P. putida* strain, it is shown herein that causal mutations are related to, among other things, PP_3350, encoding a hypothetical protein.

TALE experiments with aromatic compounds were performed by cultivating six independent parallel biological replicates of *P. putida* in minimal media supplemented with pCA, FA, or an equal mass mixture of pCA and FA ("pCA+FA") until the growth rate reached 0.15 $h^{-1}$, at which point the cells were propagated into media with an increased substrate concentration (FIGS. 2A through 2I). Additionally, ALE was performed with *P. putida* propagated in minimal media supplemented with a static concentration of glucose to identify general adaptation to media components and/or the cultivation conditions in four biological replicates (FIG. 1).

Figure 3A:
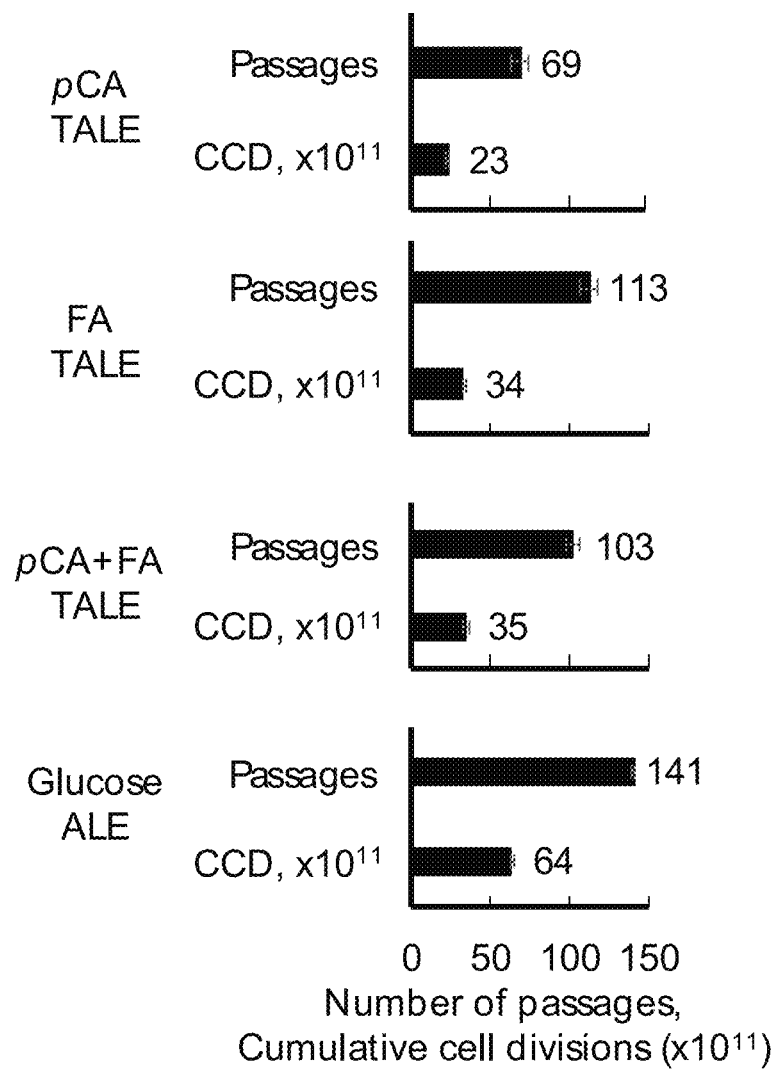
FIGS. 3A, 3B, and 3C depict experimental and growth parameters for p-coumarate (pCA) tolerance adaptive laboratory evolution (TALE), ferulate (FA) TALE, equal mass mixture pCA and FA (pCA+FA) TALE, and glucose adaptive laboratory evolution (ALE).
Figure 3B:
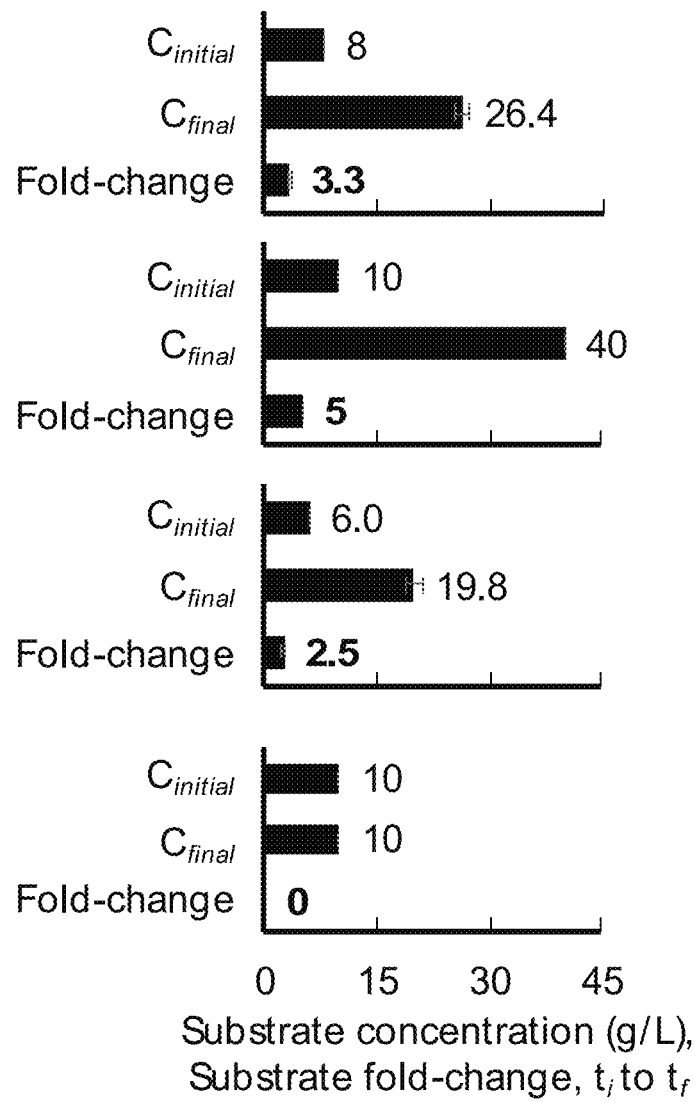
Figure 3C:
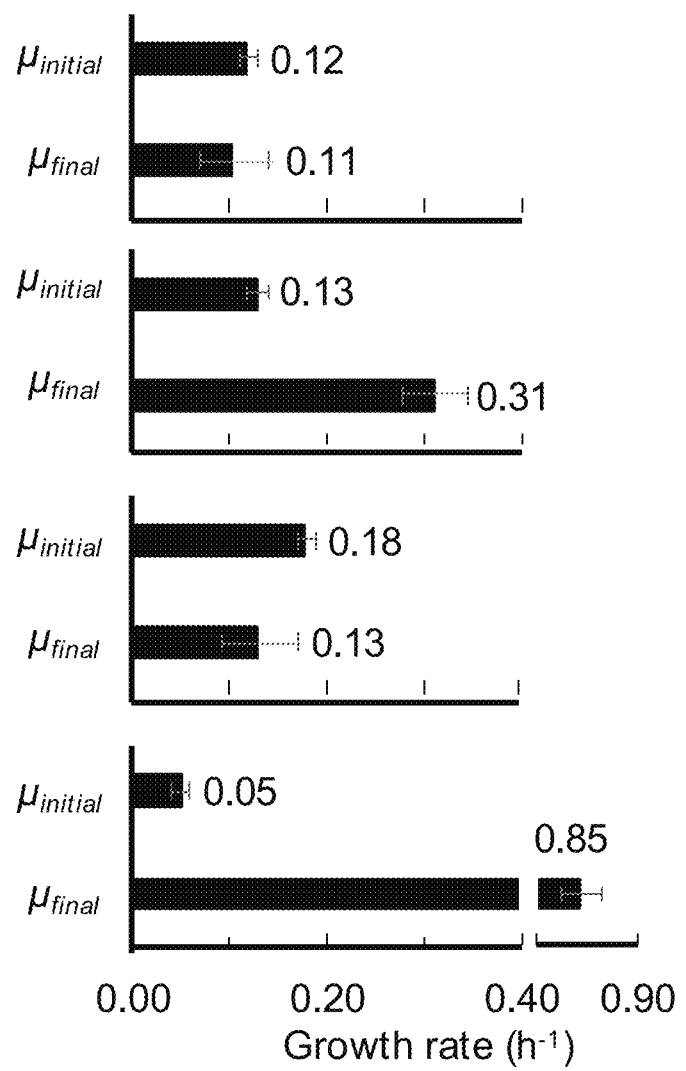

The aromatic TALEs were passaged 69 to 113 times, enabling evolution over 23-35×$10^{11}$ cumulative cell divisions (CCDs) (FIGS. 3A, 3B, and 3C, FIGS. 2A-2I). By the final passage evolved *P. putida* cells had developed the capacity to grow in a 3.3-, 5.0-, and 2.5-fold increase in concentration of pCA, FA, and pCA+FA, respectively (FIG. 3B). The final growth rate increased in FA TALEs but not pCA or pCA+FA (FIG. 3C), suggesting that the fitness advantage acquired by *P. putida* evolved in pCA TALEs was primarily tolerance whereas *P. putida* evolved in FA TALEs acquired both improved tolerance and utilization capacity. The four independent and parallel glucose ALEs progressed much faster and further than the aromatic TALES, achieving 64×$10^{11}$ CCDs and a substantial growth rate improvement (FIGS. 3A, 3B, and 3C). The increase in growth rate observed in glucose ALEs occurred within the first third of the experiment and then plateaued (FIG. 1) whereas all of the aromatic TALEs displayed oscillatory growth rate increases/decreases (FIGS. 2A through 2I), indicating that continual adaptation was occurring in dynamic TALEs but not in static ALEs.

Figure 4A:
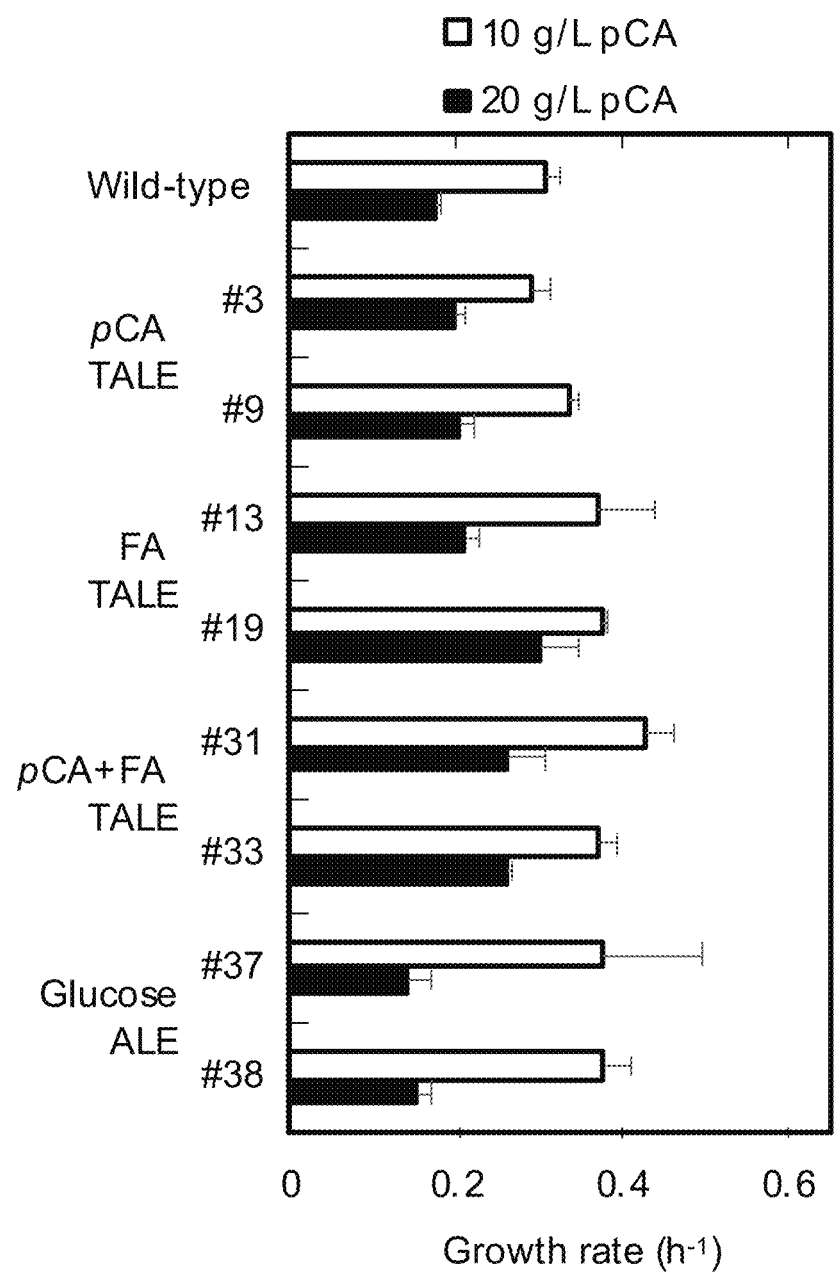
FIGS. 4A, 4B, 4C, and 4D depict population screen of wild-type *P. putida* and evolved populations from p-coumararte (pCA TALE #3 and TALE #9), ferulate (FA TALE #13 and TALE #19), equal mass mixture of p-coumarate and ferulate (pCA+FA TALE #31 and TALE #37) TALES and glucose (Glucose ALE #37 and ALE #38) taken at the endpoint. Growth rates from test tube cultivations in M9 minimal media supplemented with (FIG. 4A) 10 g/L pCA or 20 g/L pCA, (FIG. 4B) 10 g/L FA or 30 g/L FA, (FIG. 4C) 10 g/LpCA+FA (5 g/L each) or 20 g/L pCA+FA (10 g/L each), and (FIG. 4D) 10 g/L glucose. Dashed grey lines are provided to aid in the visual comparison of mutant values to wild-type values. Error bars represent the absolute difference between biological duplicates.

Next, population screens were performed to determine if the growth rate increase observed in TALE experiments could be recapitulated in the endpoint populations. Two endpoint populations were selected per TALE, cultivated in test tubes alongside the parent wild-type P. putida, and the growth rates were compared to assess catabolic capacity on the different substrates, independently if the strains were or not evolved in that specific substrate FIGS. 4A, 4B, 4C, and 4D). Growth rate improvements on pCA were modest (FIG. 4A), which is agreement with the TALE measurements (FIG. 3C). Interestingly, FA TALEs were more successful at improving pCA catabolic capacity than pCA TALEs (FIG. 4a. Dramatic growth rate improvements were observed on FA from all evolved populations except those on glucose ALE experiments, respectively. In each TALE and ALE experiment, over 70% of the mutations were single nucleotide polymorphisms (SNPs) with insertion and deletion prevalence varying by experiment (FIG. 5).

Figure 6:
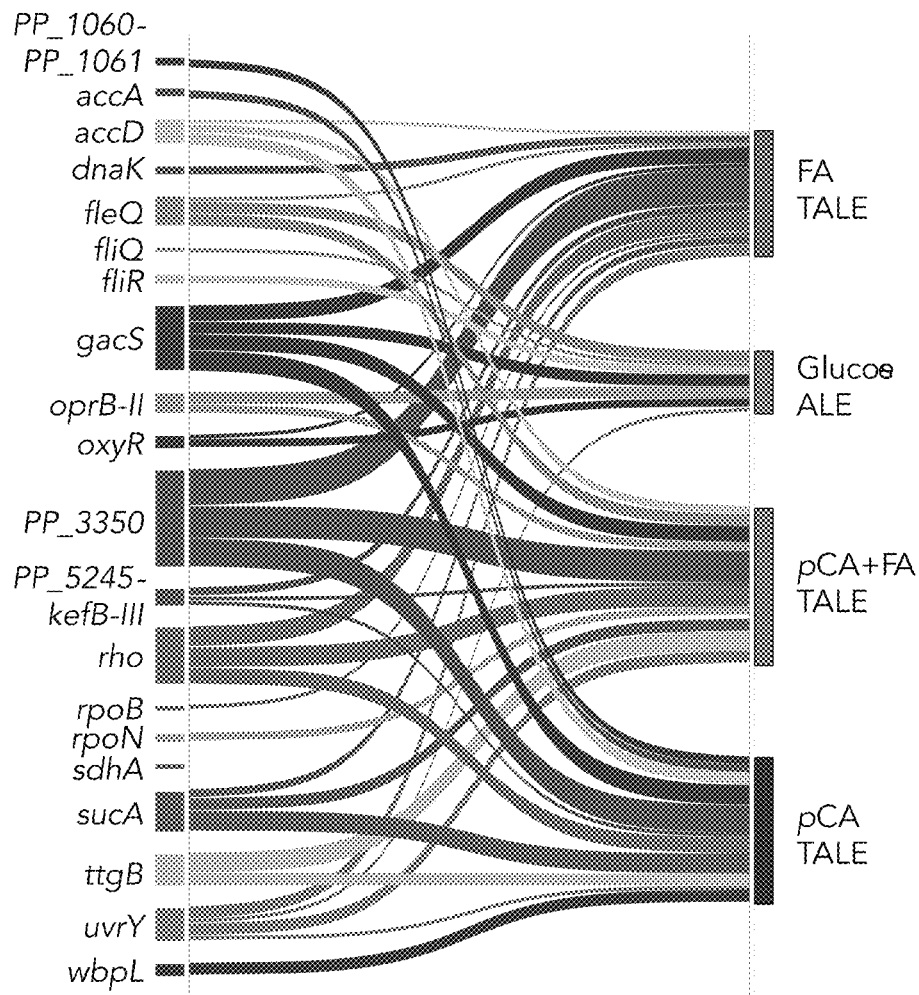
FIG. 6 depicts *putida* from pCA, FA, and pCA+FA TALEs or glucose ALE. Genes/genetic loci are listed on the left-hand side. Line width is proportional to the number of unique occurrences in which a given gene or genetic region was mutated. See Table 1 for another depiction of converged mutations.

Converged mutations were identified by comparing all clonal and population samples and selecting genes which presented a mutation in >2 independent TALE or ALE experiments, either replicates on the same carbon source or in a different carbon source. Several genes were mutated in more than one of the aromatic TALEs but not the glucose ALE, including sucA, rho, PP_3350, ttgB, accD, and the intergenic region between PP_5245 and kefB-III (FIG. 6, Table 1). Many of the converged mutations from glucose ALEs were shared with at least one of the aromatic TALEs (FIG. 6, Table 1) implying that these adaptations are related to the cultivation conditions rather than the carbon source.

TABLE 1

Converged mutations identified in P. putida from pCA, FA, and pCA+FA TALEs or glucose ALE.

| Gene/ Region | Mutation type† (unique counts) | Gene annotation(s)‡ | Experiment(s) in which mutations were identified¥ |
|---|---|---|---|
| gacS | SNP (7), DEL (3) | sensor protein GacS | pCA, FA, pCA + FA, Glucose |
| oprB-II | SNP (2), DEL (1) | carbohydrate-selective porin | pCA + FA, Glucose |
| uvrY | SNP (6), INS (1) | BarA/UvrY two-component system response regulator | pCA, FA, pCA + FA, Glucose |
| sucA | SNP (7) | 2-oxoglutarate dehydrogenase subunit E1 | pCA, FA, pCA + FA |
| rho | SNP (10) | transcription termination factor Rho | pCA, FA, pCA + FA |
| PP_3350 | SNP (6), DEL (12), INS/DUP (3), INS (1) | hypothetical protein | pCA, FA, pCA + FA |
| ttgB | SNP (6) | efflux pump membrane protein TtgB | pCA, pCA + FA |
| accD | SNP (3) | acetyl-CoA carboxylase carboxyltransferase subunit beta | pCA, FA, pCA + FA |
| PP_5245, kefB-III | SNP (2) | AraC family transcriptional regulator/glutathione-regulated potassium/H+ antiporter | pCA, FA, pCA + FA |
| fleQ | SNP (6), DEL (1) | transcriptional regulator FleQ | FA, pCA + FA, Glucose |
| accA | SNP (2) | acetyl-CoA carboxylase carboxyltransferase subunit alpha | pCA |
| dnak | SNP (2) | chaperone protein Dnak | FA |
| wbpL | SNP (1), INS (2) | glycosyl transferase WbpL | pCA |
| PP_1060, PP_1061 | SNP (2) | glutamate synthase large subunit/ATP-dependent DNA helicase | PCA |
| rpoN | INS (1), DEL (1) | RNA polymerase sigma-54 factor | pCA + FA |
| sdhA | SNP (1) | succinate dehydrogenase flavoprotein subunit | pCA + FA |
| oxyR | SNP (1), INS/DUP (1) | oxidative and nitrosative stress transcriptional dual regulator | Glucose |
| fliR | DUP (1) | flagellar biosynthetic protein FliR | Glucose |

†Mutation type abbreviations: SNP, single nucleotide polymorphism; INS, insertion; DEL, deletion; DUP: duplication.
‡Annotations assigned from NCBI Reference Genome NC_002947.X
¥Experiment abbreviations: pCA, TALE in p-coumaric acid; FA, TALE in ferulic acid; pCA + FA, TALE in equimass mixture of p-coumaric acid and ferulic acid; Glucose, ALE in glucose.

Figure 4B:
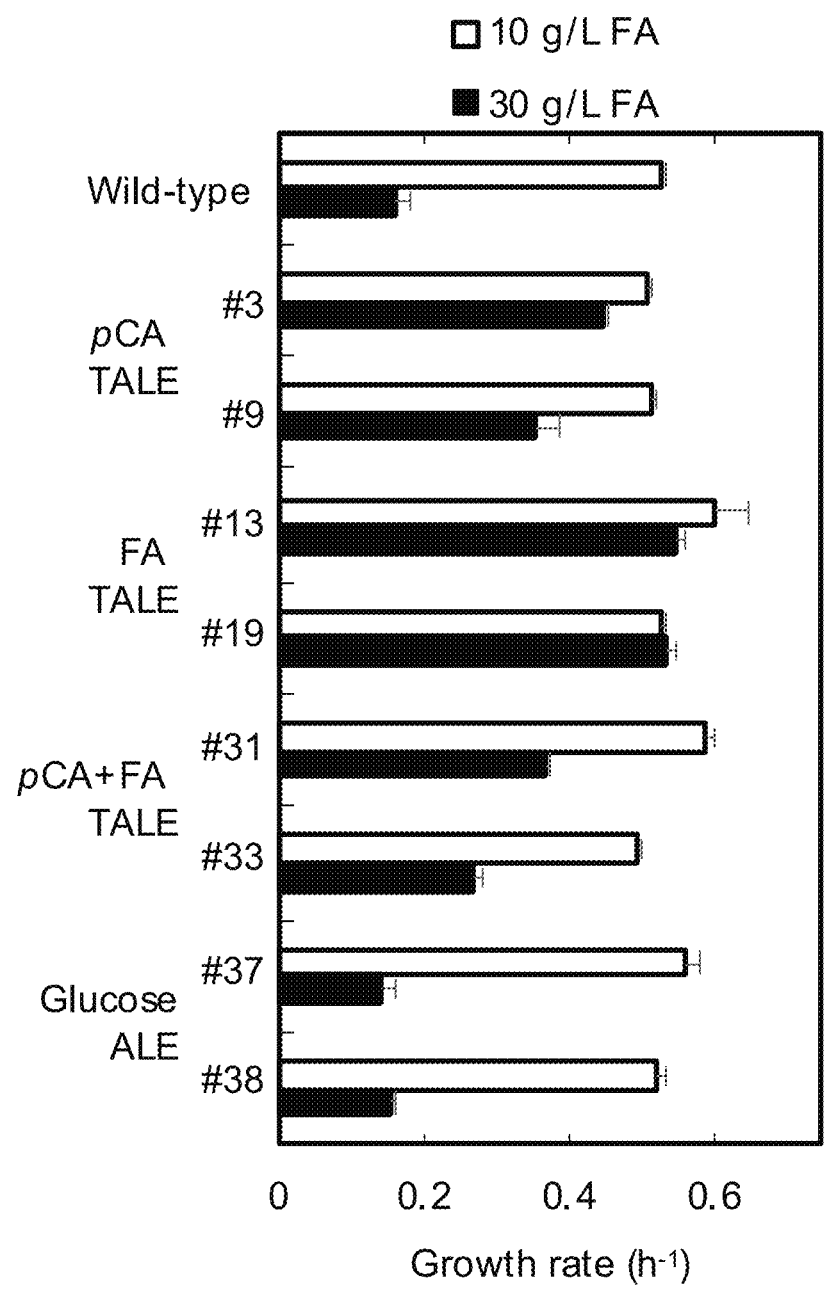
Figure 4C:
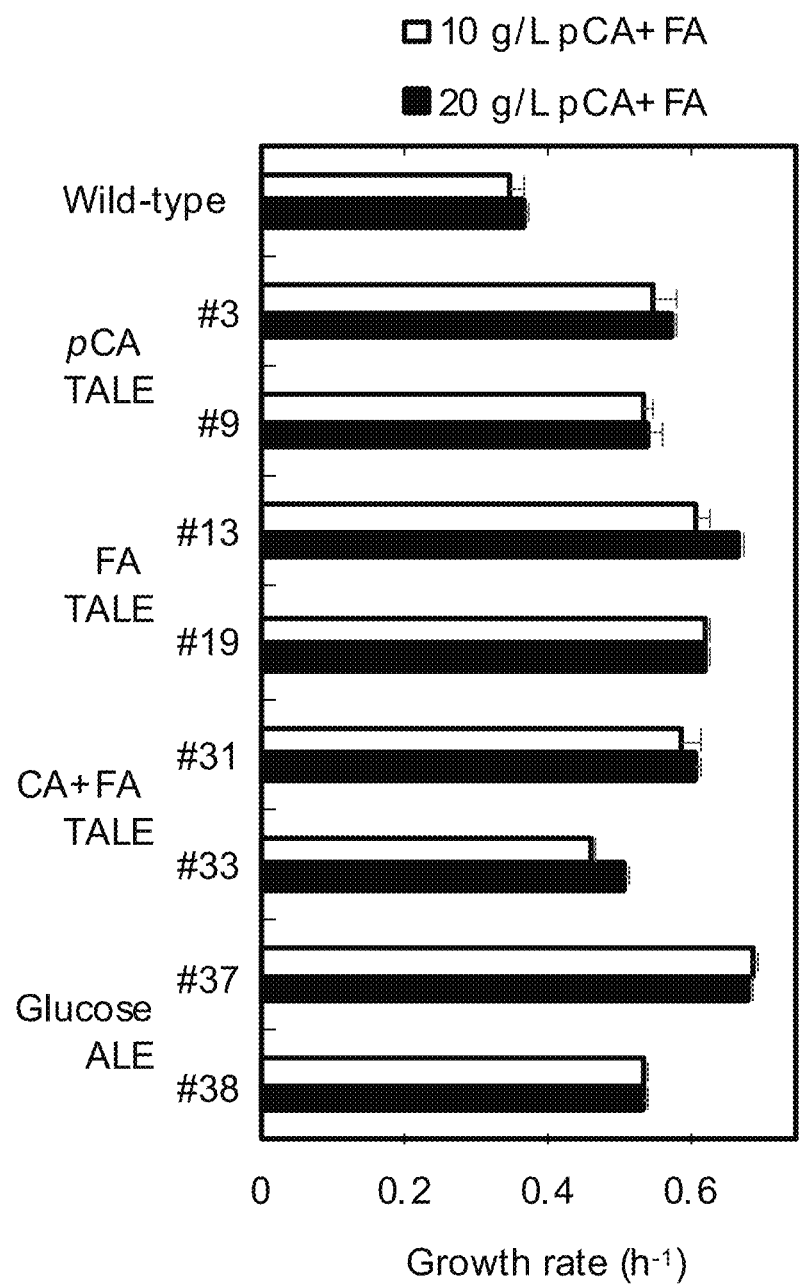
Figure 4D:
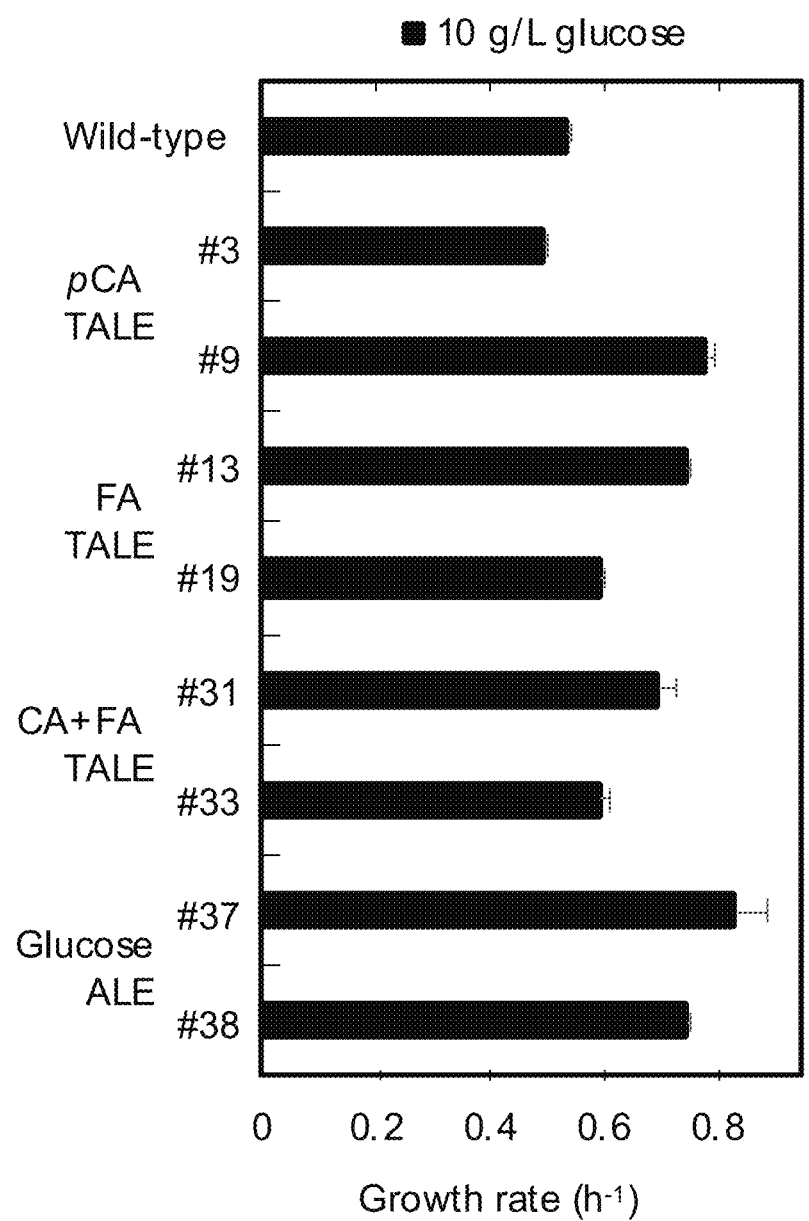
Figure 5:
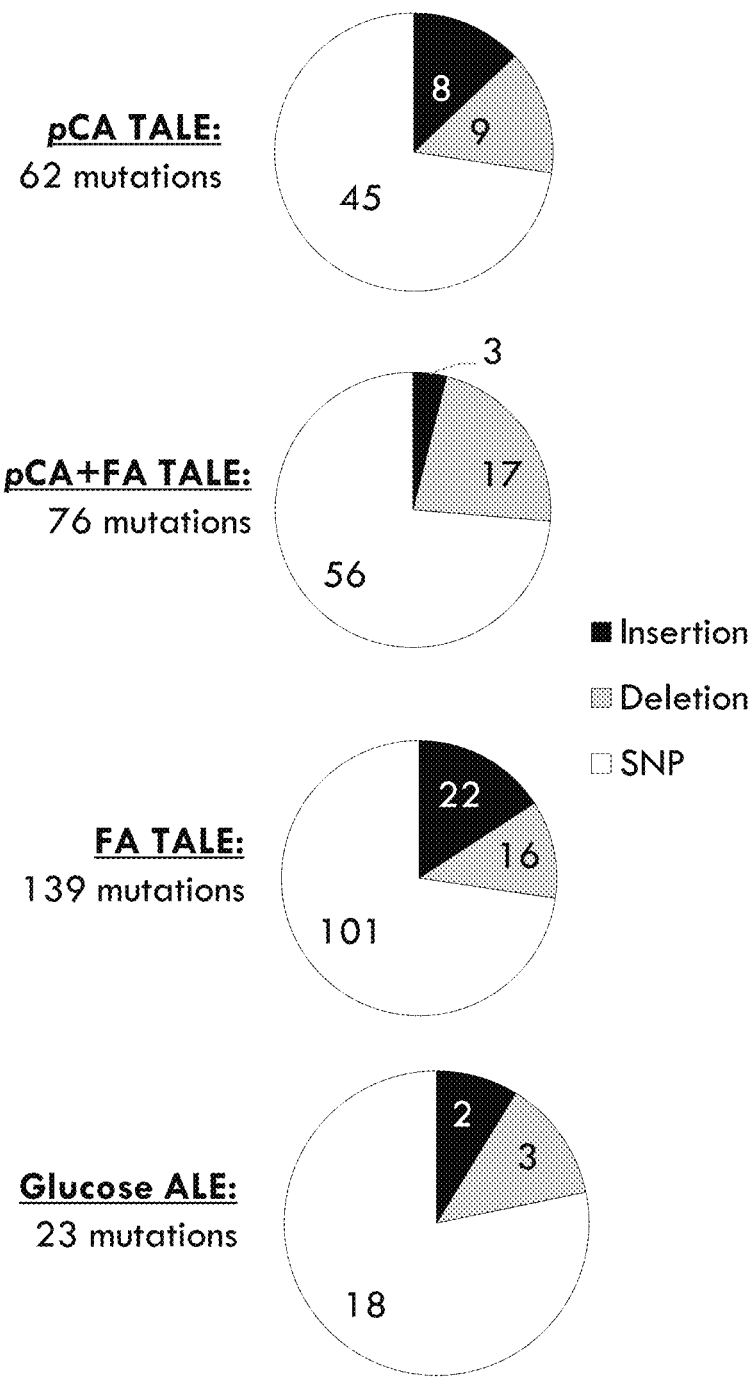
FIG. 5 depicts the total number and types of unique mutations identified in pCA TALE, FA TALE, pCA+FA TALE (equal mass mixture), or glucose ALE. Abbreviations: pCA, p-coumaric acid; FA, ferulic acid; SNP, single nucleotide polymorphism.

(FIG. 4B). However, glucose-evolved strains performed better than wild-type on pCA+FA (FIG. 4C) and most of the evolved populations performed better than wild-type on glucose (FIG. 4D). Together these data suggest that mutations acquired by evolved populations cause both general adaptation to the cultivation conditions as well as increased FA and pCA catabolic capacity.

To identify mutations which may contribute to the improved phenotype in evolved populations, whole genome resequencing was performed on three isolates and the endpoint population from intermediate and endpoint flasks for each TALE and ALE experiment. Strain-specific mutations and poor reads were filtered. In total, 62, 139, 76, and 23 mutations were identified in clonal isolates or populations from pCA TALE, FA TALE, pCA+FA TALE, and glucose Next, individual mutations that underlie the improved phenotypes were identified. One of the most frequently mutated genes in pCA, FA, and pCA+FA TALEs was PP_3350, encoding a hypothetical protein (Table 1,). PP_3350 was mutated extensively with SNPs, insertions, and deletions in pCA, FA, and pCA+FA TALEs. Accordingly, it was hypothesized that deletion of PP_3350 would improve growth in pCA and/or FA. To test this hypothesis a single-gene deletion was constructed in wild-type P. putida of PP_3350 (strain CJ782) and growth was examined alongside endpoint populations which harbored the mutation in the corresponding gene.

The effect of PP_3350 deletions on growth on hydroxycinnamic acids was evaluated. PP_3350 is a hypothetical protein which harbors an 18 stranded ß-barrel pore domain with homology to porins involved in alginate export. Endpoint populations from pCA TALE #7, FA TALE #23, and pCA+FA TALE #25 were selected for comparison with wild-type and CJ782 as they each harbor PP_3350 deletions of varying length in addition to other mutations (FIGS. 7A, 7B, 7C, and 7D, Table 2). Growth was evaluated in "low" (10 g/L) and "high" (20 g/L for pCA and 30 g/L for FA) substrate concentrations corresponding to the starting and late substrate levels, respectively, in the evolution experiment (FIGS. 2A through 2I, FIG. 3B). Growth rate was calculated to compare catabolic capacity and lag phase was calculated to evaluate substrate toxicity tolerance.

TABLE 2

Description of strains

| Strain name | Description | Reference |
|---|---|---|
| Wild-type P. putida | Pseudomonas putida KT2440 kindly provided by Pablo I. Nikel | ATCC® 47054™ |
| CJ782 | Pseudomonas putida KT2440 ΔPP_3350 | This study |
| MJD1 | Pseudomonas putida KT2440 ΔttgB | This study |
| TALE#1 | Pseudomonas putida KT2440 subjected to TALE in p-coumaric acid, replicate #1, mixed population | This study |
| TALE#3 | Pseudomonas putida KT2440 subjected to TALE in p-coumaric acid, replicate #2, mixed population | This study |
| TALE#5 | Pseudomonas putida KT2440 subjected to TALE in p-coumaric acid, replicate #3, mixed population | This study |
| TALE#7 | Pseudomonas putida KT2440 subjected to TALE in p-coumaric acid, replicate #4, mixed population | This study |
| TALE#9 | Pseudomonas putida KT2440 subjected to TALE in p-coumaric acid, replicate #5, mixed population | This study |
| TALE#11 | Pseudomonas putida KT2440 subjected to TALE in p-coumaric acid, replicate #6, mixed population | This study |
| TALE#13 | Pseudomonas putida KT2440 subjected to TALE in ferulic acid, replicate #1, mixed population | This study |
| TALE#15 | Pseudomonas putida KT2440 subjected to TALE in ferulic acid, replicate #2, mixed population | This study |
| TALE#17 | Pseudomonas putida KT2440 subjected to TALE in ferulic acid, replicate #3, mixed population | This study |
| TALE#19 | Pseudomonas putida KT2440 subjected to TALE in ferulic acid, replicate #4, mixed population | This study |
| TALE#21 | Pseudomonas putida KT2440 subjected to TALE in ferulic acid, replicate #5, mixed population | This study |
| TALE#23 | Pseudomonas putida KT2440 subjected to TALE in ferulic acid, replicate #6, mixed population | This study |
| TALE#25 | Pseudomonas putida KT2440 subjected to TALE in an equal mass mixture of p-coumaric acid and ferulic acid, replicate #1, mixed population | This study |
| TALE#27 | Pseudomonas putida KT2440 subjected to TALE in an equal mass mixture of p-coumaric acid and ferulic acid, replicate #2, mixed population | This study |
| TALE#29 | Pseudomonas putida KT2440 subjected to TALE in an equal mass mixture of p-coumaric acid and ferulic acid, replicate #3, mixed population | This study |
| TALE#31 | Pseudomonas putida KT2440 subjected to TALE in an equal mass mixture of p-coumaric acid and ferulic acid, replicate #4, mixed population | This study |
| TALE#33 | Pseudomonas putida KT2440 subjected to TALE in an equal mass mixture of p-coumaric acid and ferulic acid, replicate #5, mixed population | This study |
| TALE#35 | Pseudomonas putida KT2440 subjected to TALE in an equal mass mixture of p-coumaric acid and ferulic acid, replicate #6, mixed population | This study |
| ALE#37 | Pseudomonas putida KT2440 subjected to ALE in glucose, replicate #1, mixed population | This study |
| ALE#38 | Pseudomonas putida KT2440 subjected to ALE in glucose, replicate #2, mixed population | This study |
| ALE#39 | Pseudomonas putida KT2440 subjected to ALE in glucose, replicate #3, mixed population | This study |
| ALE#40 | Pseudomonas putida KT2440 subjected to ALE in glucose, replicate #4, mixed population | This study |
| MJD2 | TALE#25 (Pseudomonas putida KT2440 subjected to TALE in an equal mass mixture of p-coumaric acid and ferulic acid, replicate #1, mixed population) ΔttgB | This study |
| MJD3 | TALE#27 (Pseudomonas putida KT2440 subjected to TALE in an equal mass mixture of p-coumaric acid and ferulic acid, replicate #2, mixed population) ΔttgB | This study |
| MJD4 | TALE#31 (Pseudomonas putida KT2440 subjected to TALE in an equal mass mixture of p-coumaric acid and ferulic acid, replicate #4, mixed population) ΔttgB | This study |

Figure 7A:
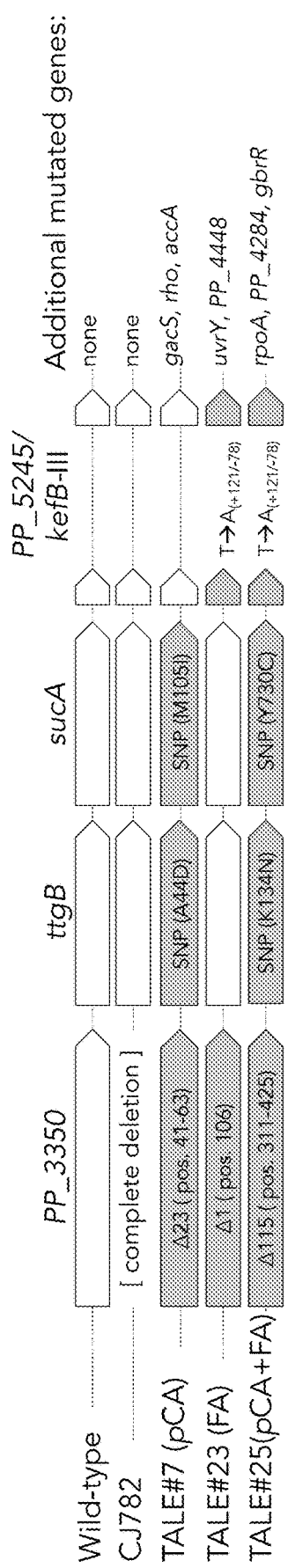
FIGS. 7A, 7B, 7C, and 7D depict Growth characteristics of *P. putida* wild-type PP_3350 mutants on pCA and/or FA as the sole carbon source.
Figure 7B:
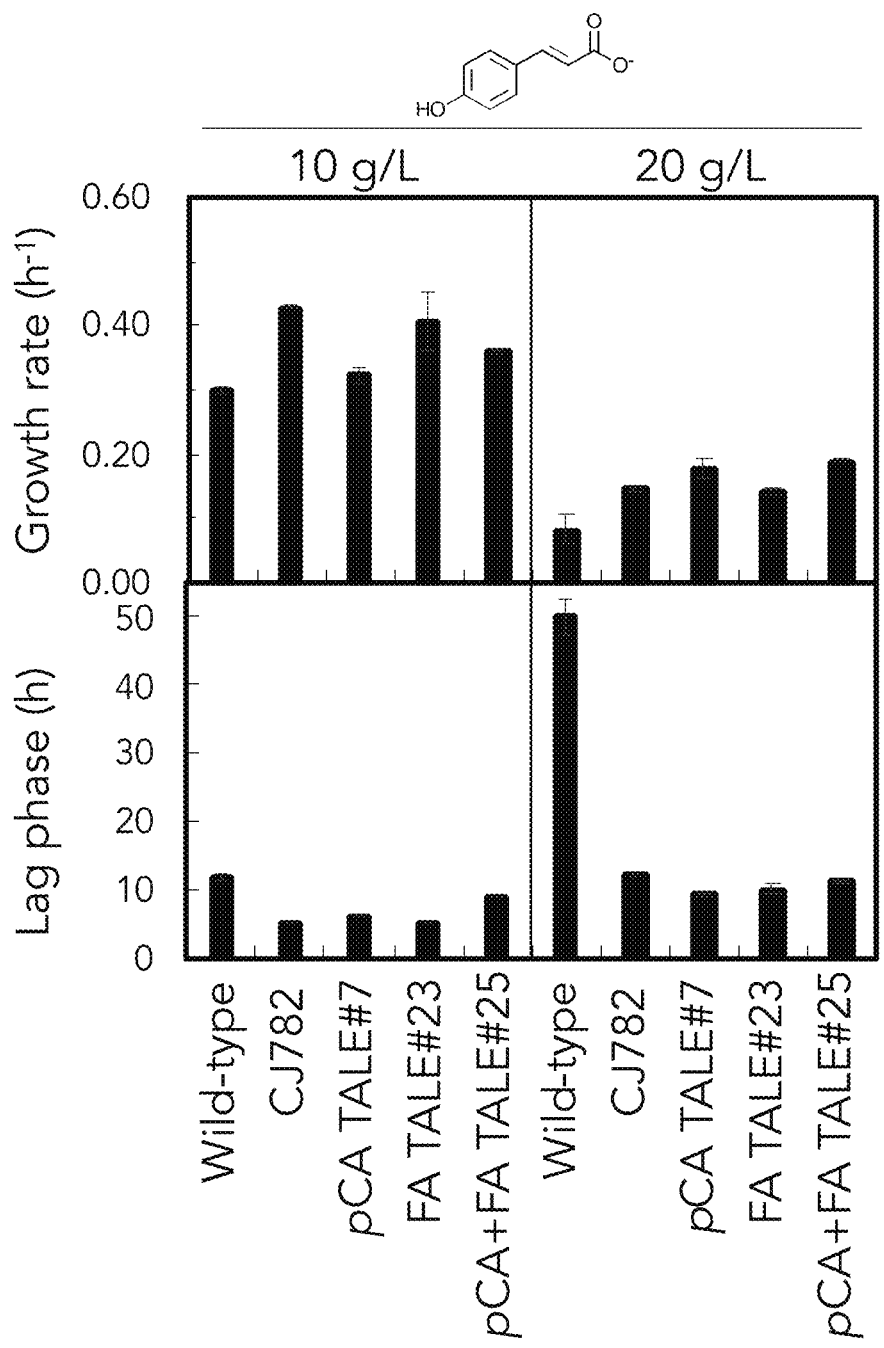
Figure 7C:
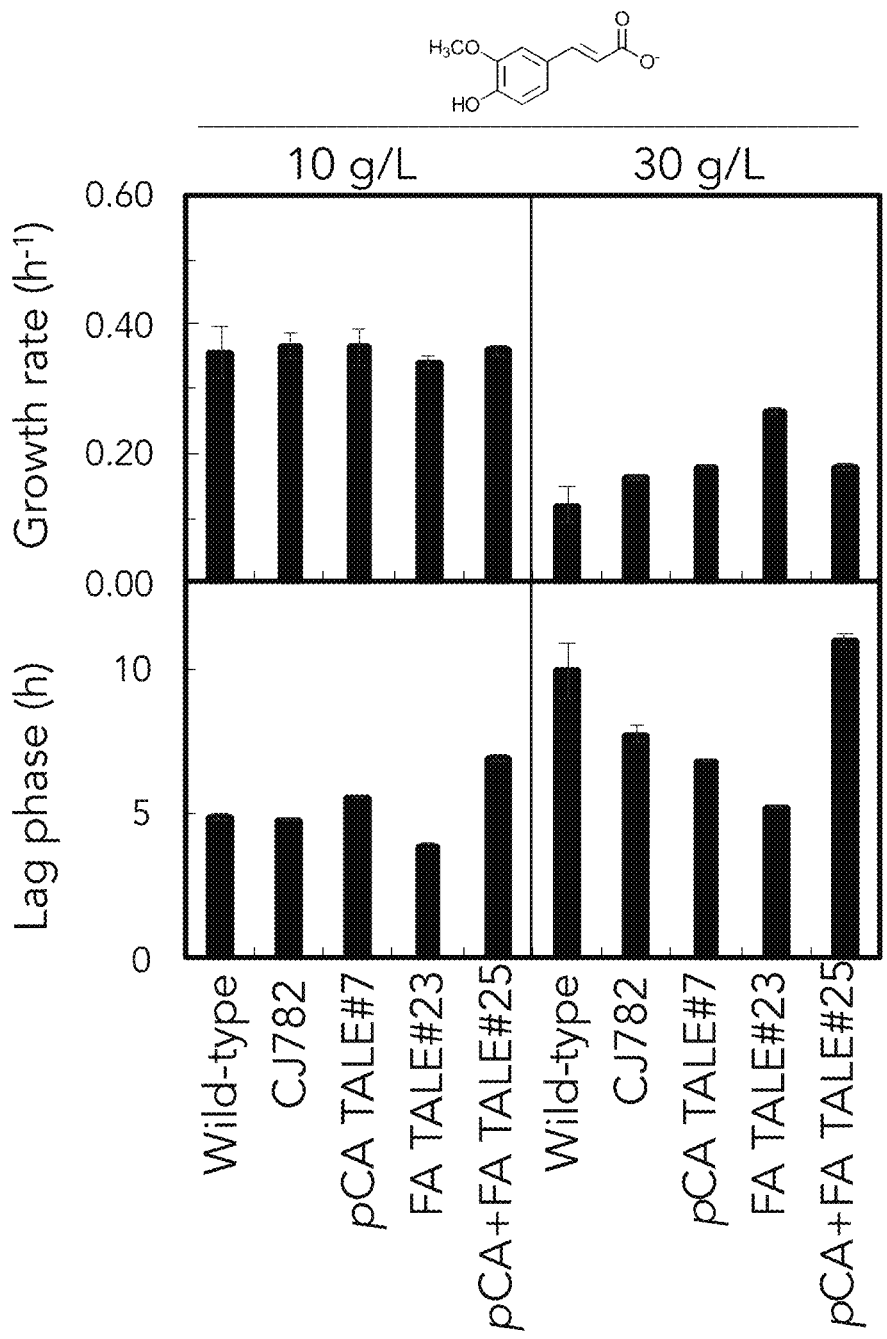
Figure 7D:
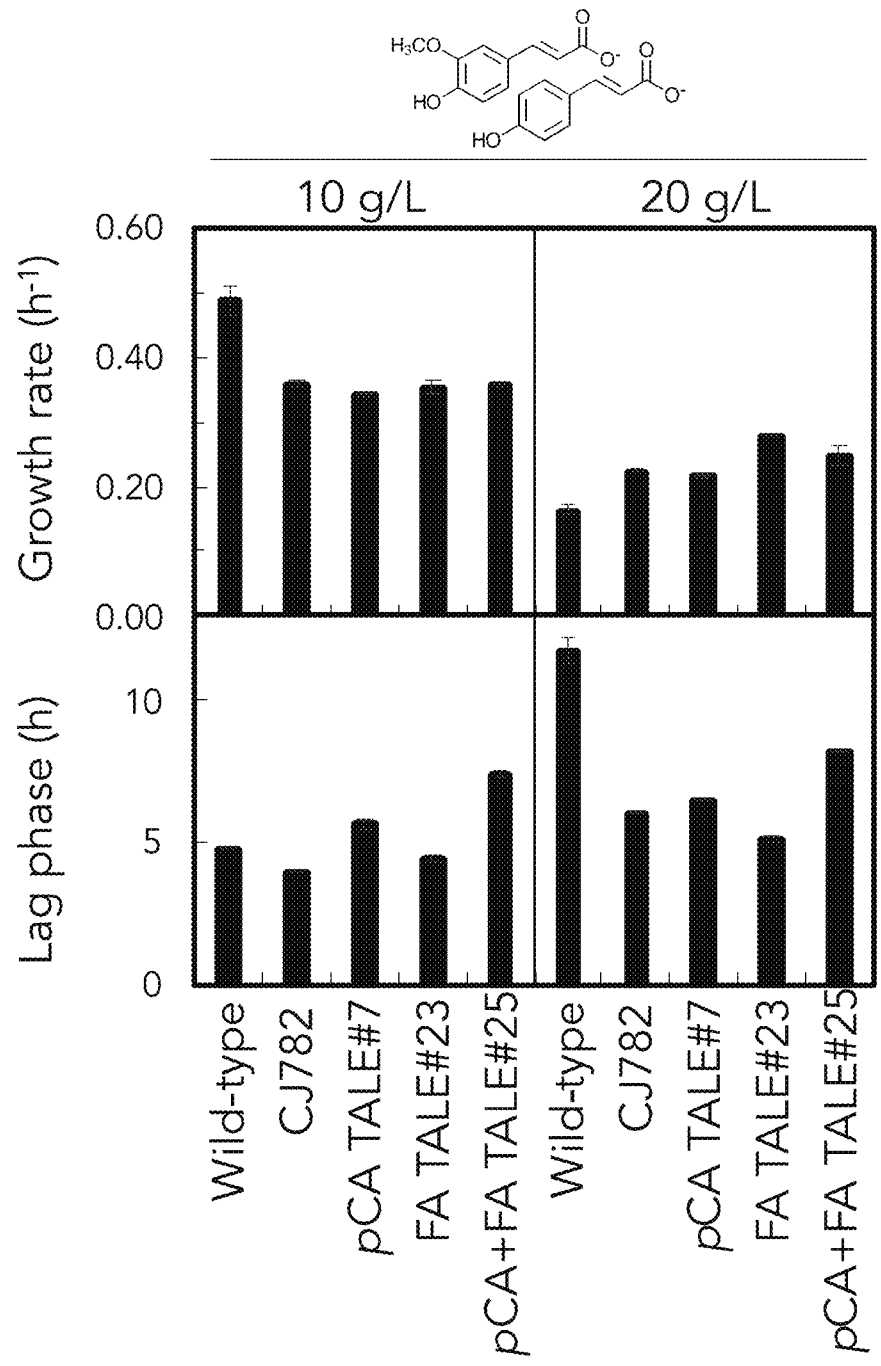

Interestingly, CJ782 and each of the TALE endpoint populations have dramatically reduced lag phases compared to wild-type in 20 g/L pCA (FIG. 7B). These strains also exhibit slightly improved growth rates compared to wild-type, but again only in the high concentration of pCA (FIG. 7B). In agreement with the parameters from TALE experiments (FIG. 3C), these data indicate that evolution—and, more specifically, the deletion of PP_3350—results in improved tolerance but not an improved growth rate in high concentrations of pCA. In 30 g/L FA, however, FA-evolved TALE #23 displays improved catabolic capacity and improved tolerance compared to wild-type P. putida (FIG. 7C). The deletion of PP_3350 does not fully recapitulate the observed phenotype in TALE #23, indicating that additional mutations present in this population may underly the improve FA catabolic capacity. Growth rate is slightly but universally decreased in CJ782 and TALE populations in 10 g/L pCA+FA (5 g/L of each compound) but slightly increased in 20 g/LpCA+FA (10 g/L of each compound, (FIG. 7D). Given that growth advantages are modest in each compound at 10 g/L alone, this suggests that the adaptations are advantageous above a given threshold of total aromatic compound. In summary, PP_3350 deletion recapitulates the improved pCA tolerance but not improved FA catabolic capacity of TALE endpoint populations.

Materials and Methods:

Strains and media: P. putida KT2440 provided by Dr. Pablo I. Nikel was cultivated in modified M9 minimal media (1×M9 salts, 2 mM MgSO$_4$, 100 µM CaCl$_2$), 1× trace elements). M9 salts (10×) consisted of 68 g/L Na$_2$HPO$_4$ anhydrous, 30 g/L KH$_2$PO$_4$, 5 g/L NaCl, and 20 g/L (NH$_4$)$_2$SO$_4$. Trace elements (2000×) consisted of 3 g/L FeSO$_4$·7H$_2$O, 4.5 g/L ZnSO$_4$·7H$_2$O, 0.3 g/L CoCl$_2$·6H$_2$O, 0.4 g/L Na$_2$MoO$_4$·2H$_2$O, 4.5 g/L CaCl$_2$·H$_2$O, 0.2 g/L CuSO$_4$·2H$_2$O, 1 g/L H$_3$BO$_3$, 15 g/L EDTA, 0.1 g/L KI, and 0.7 g/L MnCl$_2$·4H$_2$O adjusted to pH 4 with HCl. pCA and FA (TCI, Belgium) stocks were prepared fresh prior to each experiment by dissolving each acid in H$_2$O and adjusting to pH 7 with NaOH. Carbon sources were added to the media in the specified concentration and the medium was sterilized by 0.22-µm filtration.

TALE and ALE experiments: The TALE and ALE experiments were conducted using an automated liquid handler platform as previously described (LaCroix et al., 2015; Mohamed et al., 2019, 2017). To prepare precultures, single isolates of P. putida on LB agar plates were inoculated at 1% (v/v) in test tubes with 15 mL M9 medium with 10 g/L glucose, 8 g/L pCA, 10 g/L FA, or 3 g/L pCA and 3 g/L FA in four biological replicates for the glucose ALE and six biological replicates for each aromatic TALE (Table 3). Cultures were incubated at 30° C. in a shaking heat block and OD$_{600}$ was measured continuously. Periodically, aliquots of cultures were sampled, mixed with 25% glycerol, and frozen at −80° C. for DNA sequencing. Whole genome sequencing and analysis: For each aromatic TALE (pCA, FA, and pCA+FA) and the glucose ALE, 1-2 intermediate isolates, the endpoint population, and a single endpoint isolate were selected and prepared for whole genome sequencing as follows. Isolates were chosen from agar plates with M9 media and the corresponding carbon source, inoculated into LB medium and cultivated overnight, genomic DNA was extracted with PureLink® Genomic DNA Extraction kit (Invitrogen, Calif., USA), quality was assessed by evaluating $Abs_{260\ nm}/Abs_{280\ nm}$ using a NanoDrop, DNA concentration was measured using a Qubit assay, and paired-end resequencing libraries were generated using the Illumina 300 cycle (150 bp×2) kit (San Diego, Calif., USA). Sequencing was performed on an Illumina NextSeq XX system (Illumina, USA). The sequencing files were analyzed using a previously described in-house script (Phaneuf et al., 2019) based on bowties2 and Breseq (version 0.30.1) and the NCBI NC 002947 reference genome for *P. putida* KT2440 was used for annotation of genes. For population samples, a filter was applied to exclude mutations with a frequency of less than 0.50, unless the same mutation was found in an isolate. Converged mutations were identified by comparing all clonal and population samples and selecting genes or genetic regions which presented a mutation in >2 independent TALE or ALE experiments, either replicates on the same carbon source or in a different carbon source.

1:100 dilution in test tubes with biological duplicates and incubated at 30° C. with aeration provided by a magnetic stir bar. $OD_{600}$ was measured using the Sunrise plate reader (Tecan Group Ltd., Switzerland).

Plasmids and strain construction: Deletion of PP_3350 was performed using the antibiotic/sacB method of gene replacement, as described previously. The plasmid pCJ222 for deleting PP_3350 was constructed by amplifying an PP_3350 homology regions by PCR from *P. putida* genomic DNA (Table 4, Table 5), assembly into the pK18sB plasmid digested with EcoRI and HindIII using NEBuilder® HiFi DNA Assembly Master Mix (New England Biolabs, USA), transformation into NEB *E. coli* DH5-alpha F'Iq cells, and the correct sequence was verified using Sanger sequencing (GENEWIZ, Germany). pCJ222 was transformed into *P. putida* as previously described and sucrose selection and diagnostic colony PCR were followed to identify a clone with proper deletion mutation. The resulting strain was named CJ782 (Table 2). When needed, antibiotics were used at the following concentrations: 30 μg/mL chloramphenicol, 50 μg/mL kanamycin, or 10 μg/mL gentamicin.

Evaluation of reverse-engineered *P. putida* ΔPP_3350 and endpoint TALE populations: Cells were revived from glyc-

TABLE 3

TALE and ALE experimental conditions. Six independent and parallel replicates were performed for the p-Coumaric acid (pCA) TALE, ferulic acid (FA) TALE, and equimolar pCA and FA TALE. Four independent and parallel replicates were performed for the glucose ALE.

| Condition | ALE # | Starting conc. (g/L) | Initial growth rate with starting conc. ($h^{-1}$) | Average ending conc. (g/L) | Final growth rate with ending conc. ($h^{-1}$)* | Fold-change in carbon source | Total number of flasks passaged | Cumulative cell division (CCD), ×$10^{12}$ | No. of cell generations |
|---|---|---|---|---|---|---|---|---|---|
| pCA TALE | 1 | 8 | 0.12 ± 0.01 | 25.6 | 0.08 | 3.20 | 62 | 2.15 | 311 |
| | 3 | | | 27.2 | 0.17 | 3.40 | 69 | 2.28 | 347.5 |
| | 5 | | | 25.6 | 0.09 | 3.20 | 73 | 2.47 | 369.5 |
| | 7 | | | 27.2 | 0.08 | 3.40 | 70 | 2.35 | 352.6 |
| | 9 | | | 27.2 | 0.09 | 3.40 | 76 | 2.43 | 381.2 |
| | 11 | | | 25.6 | 0.12 | 3.20 | 66 | 2.18 | 336 |
| | AVG | | | 26.40 | 0.11 | 3.30 | 69.33 | 2.31 | 349.63 |
| | STDEV | | | 0.88 | 0.04 | 0.11 | 4.97 | 0.13 | 24.83 |
| FA TALE | 13 | 10 | 0.13 ± 0.01 | 40 | 0.26 | 4.00 | 104 | 3.09 | 574.3 |
| | 15 | | | 40 | 0.29 | 4.00 | 115 | 3.49 | 622.5 |
| | 17 | | | 40 | 0.34 | 4.00 | 108 | 3.42 | 594.8 |
| | 19 | | | 40 | 0.34 | 4.00 | 120 | 3.39 | 658.4 |
| | 21 | | | 40 | 0.34 | 4.00 | 114 | 3.33 | 622.8 |
| | 23 | | | 40 | 0.31 | 4.00 | 115 | 3.49 | 632.5 |
| | AVG | | | 40.00 | 0.31 | 4.00 | 112.67 | 3.37 | 617.55 |
| | STDEV | | | 0.00 | 0.03 | 0.00 | 5.72 | 0.15 | 29.44 |
| pCA + FA TALE | 25 | 6 | 0.18 ± 0.01 | 20.4 | 0.12 | 3.40 | 98 | 3.42 | 602.4 |
| | 27 | | | 20.4 | 0.11 | 3.40 | 104 | 3.63 | 538.6 |
| | 29 | | | 20.4 | 0.08 | 3.40 | 104 | 3.44 | 535 |
| | 31 | | | 20.4 | 0.12 | 3.40 | 103 | 3.51 | 531.5 |
| | 33 | | | 17.5 | 0.18 | 2.92 | 109 | 3.69 | 558.7 |
| | 35 | | | 19.8 | 0.18 | 3.30 | 97 | 3.16 | 493.3 |
| | AVG | | | 19.82 | 0.13 | 3.30 | 102.50 | 3.48 | 543.25 |
| | STDEV | | | 1.16 | 0.04 | 0.19 | 4.42 | 0.19 | 35.94 |
| Glucose ALE | 37 | 10 | 0.50 ± 0.01 | 10 | 0.83 | 0 | 141 | 6.36 | 917.8 |
| | 38 | (constant) | | (constant) | 0.85 | | 143 | 6.53 | 934.9 |
| | 39 | | | | 0.87 | | 141 | 6.37 | 919.5 |
| | 40 | | | | 0.83 | | 140 | 6.43 | 913.5 |
| | AVG | | | | 0.85 | | 141.25 | 6.42 | 921.43 |
| | STDEV | | | | 0.02 | | 1.26 | 0.08 | 9.33 |

Evaluation of TALE endpoint populations: Cells were revived from glycerol stocks on M9 minimal media plates supplemented with 5 g/L of the carbon compound(s) from which the populations were evolved, inoculated into 15 mL of M9 minimal medium containing 5 g/L of the same aromatic compound used in the plates, and incubated at 30° C., 1100 rpm until the $OD_{600}$ reached 3.0. Cells were inoculated into fresh M9 minimal medium supplemented with the carbon source specified in each experiment at a erol stocks in 50 mL M9 minimal medium supplemented with 3 g/L of the aromatic compound from which the populations were evolved or 10 g/L glucose in baffled flasks and incubated at 30° C. and 225 rpm until the $OD_{600}$ reached 3.0. Cells were inoculated in fresh medium to an $OD_{600}$ in 300 μL and incubated in 100-well honeycomb plates in a BioscreenC™ (Growth Curves USA, USA) at 30° C., maximum continuous shaking, and $Abs_{420-580}$ measurements were taken every 15 minutes.

TABLE 4

Primers

| Primer name | Primer sequence, 5' → 3' | Purpose |
| --- | --- | --- |
| oCJ680 (SEQ ID NO: 3) | TTTGTGATGCTCGTCAGGG | Sequencing a pK18sB insert |
| oCJ681 (SEQ ID NO: 4) | CTTCCCAACCTTACCAGAG | Sequencing a pK18sB insert |
| oCJ791 (SEQ ID NO: 5) | ACATGATTACGAATTCCGGACATCAGCATCGC | Amplifying the upstream targeting region for PP_3350 |
| oCJ792 (SEQ ID NO: 6) | TTAAACACTTGTTTTTATAATTGTTCTTACAAACTGG | |
| oCJ793 (SEQ ID NO: 7) | TTATAAAAACAAGTGTTTAAACCCACCCGACCGATAACAAC | Amplifying the downstream targeting region for PP_3350 |
| oCJ794 (SEQ ID NO: 8) | TGCCAAGCTTTCAGCGACGCAACCGC | |
| oCJ795 (SEQ ID NO: 9) | GTCTCCGACATCATGCCCAGC | Confirming deletion of PP_3350 by colony PCR |
| oCJ796 (SEQ ID NO: 10) | GTAGAACACCGTACGCCAACCG | |
| TEAM-1640 (SEQ ID NO: 11) | ACCCACCGCCCTGGTGGTCAACC | Confirming deletion of PP_1385 (ttgB) by colony PCR (outside-outside pair) |
| TEAM-1641 (SEQ ID NO: 12) | CAGGGATCAGCGAGCAGCCGCCAAG | |
| F-5'ttgAend (SEQ ID NO: 13) | CGTCGAGGTGAAGGTCAGCGATGC | Confirming deletion of ttgB in TALE knockouts |
| RttgCbeg (SEQ ID NO: 14) | CCGATTGCGTCGGCGAGATAAGCAG | |

TABLE 5

Plasmids

| Plasmid name | Purpose | Reference |
| --- | --- | --- |
| pK18mobsacB | Non-replicative kanR sacS; allelic exchange plasmid in P. putida KT2440 | GenBank: MH166772 |
| pCJ222 | Deletion of PP_3350 from the chromosome of P. putida KT2440 | This study |
| pK18mosacB | Non-replicative kanR sacS; allelic exchange plasmid in P. putida KT2440 | (Schäfer et al. 1994) |
| pTE289 | For the deletion of ttgB (ΔPP_1385) from the chromosome of P. putida KT2440 | This study |

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A genetically modified *Pseudomonas* comprising:
   a mutation of a gene encoding a cell membrane protein wherein:
   the mutation improves tolerance to a hydroxycinnamic acid, and
   the gene encodes for a protein that is at least 92% identical to SEQ ID NO: 2.

2. The genetically modified *Pseudomonas* of claim 1 capable of converting hydroxycinnamic acid to muconate.

3. The genetically modified *Pseudomonas* of claim 1 wherein the mutation of a gene encoding a cell membrane protein decreases the time that the *Pseudomonas* spends in a lag phase when exposed to a solution of hydroxycinnamic acid compared to a non-genetically modified *Pseudomonas*.

4. The genetically modified *Pseudomonas* of claim 1 wherein the mutation increases a growth rate of the *Pseudomonas* when exposed to a solution of hydroxycinnamic acid compared to a non-genetically modified *Pseudomonas*.

5. The genetically modified *Pseudomonas* of claim 1, wherein the gene is at least 92% identical to SEQ ID NO: 1.

6. The genetically modified *Pseudomonas* of claim 1, wherein the hydroxycinnamic acid is selected from the group consisting of coumarate and ferulate.

7. The genetically modified *Pseudomonas* of claim 1, wherein the *Pseudomonas* is *P. putida* K2440.

8. The genetically modified *Pseudomonas* of claim 1, wherein the *Pseudomonas* demonstrates at least a 3.3-fold increased tolerance to p-coumaric acid (pCA) compared to a non-genetically modified *Pseudomonas*.

9. The genetically modified *Pseudomonas* of claim 1, wherein the *Pseudomonas* has at least a 37 hour decrease in lag phase when exposed to 20 g/L pCA compared to a non-genetically modified *Pseudomonas*.

10. The genetically modified *Pseudomonas* of claim 1, wherein the *Pseudomonas* has at least a 2.4-fold increased growth rate when exposed to 20 g/L pCA compared to a non-genetically modified *Pseudomonas*.

11. A method for lignin valorization, the method comprising:
    converting a hydroxycinnamic acid to muconate by contacting the hydroxycinnamic acid with a genetically modified *Pseudomonas*, wherein:
    the *Pseudomonas* comprises a mutation of a gene encoding a cell membrane protein,
    the modification increases the uptake of the hydroxycinnamic acid compared to a non-genetically modified *Pseudomonas*, and
    the gene encodes for a protein that is at least 92% identical to SEQ ID NO: 2.

12. The method of claim 11 wherein the mutation decreases the time in a lag phase of the *Pseudomonas* when the *Pseudomonas* is exposed to a solution of hydroxycinnamic acid compared to a non-genetically modified *Pseudomonas*.

13. The method of claim 11 wherein the mutation increases a growth rate of the *Pseudomonas* when exposed to a solution of hydroxycinnamic acid compared to a non-genetically modified *Pseudomonas*.

14. The method of claim 11 wherein the mutation is to a gene that is at least 92% identical to SEQ ID NO: 1.

15. The method of claim 11 wherein the hydroxycinnamic acid is selected from the group consisting of coumarate, and ferulate.

16. The method of claim 11 wherein the *Pseudomonas* has at least a 3.3-fold increased tolerance to pCA, at least a 37 hour decrease in lag phase, and a 2.4-fold increased growth rate when exposed to 20 g/L pCA compared to a non-genetically modified *Pseudomonas*.

17. A genetically modified *Pseudomonas* comprising:
   a deletion of a gene encoding a cell membrane protein, wherein:
   the deletion improves tolerance to a hydroxycinnamic acid, and
   the deleted gene encodes for the expression of protein PP_3350.

18. A method for lignin valorization, the method comprising:
   converting a hydroxycinnamic acid to muconate by contacting the hydroxycinnamic acid with a genetically modified *Pseudomonas*, wherein:
   the *Pseudomonas* comprises a deletion of a gene encoding a cell membrane protein,
   the modification increases the uptake of the hydroxycinnamic acid compared to a non-genetically modified *Pseudomonas*, and
   the deleted gene encodes for the expression of protein PP_3350.

* * * * *